(12) United States Patent
Liu

(10) Patent No.: US 7,476,734 B2
(45) Date of Patent: Jan. 13, 2009

(54) NUCLEOTIDE ANALOGS

(75) Inventor: David R. Liu, Lexington, MA (US)

(73) Assignee: Helicos Biosciences Corporation, Cambridge, MA (US)

( * ) Notice: Subject to any disclaimer, the term of this patent is extended or adjusted under 35 U.S.C. 154(b) by 145 days.

(21) Appl. No.: 11/295,155

(22) Filed: Dec. 6, 2005

(65) Prior Publication Data

US 2007/0128614 A1 Jun. 7, 2007

(51) Int. Cl.
*C07H 19/04* (2006.01)
*C07H 19/20* (2006.01)
(52) U.S. Cl. .................. 536/26.21; 536/22.1; 536/25.3; 536/25.32; 536/26.1; 536/26.2
(58) Field of Classification Search ........................ None
See application file for complete search history.

(56) References Cited

U.S. PATENT DOCUMENTS

| | | | |
|---|---|---|---|
| 3,996,345 A | 12/1976 | Ullman et al. |
| 4,119,368 A | 10/1978 | Yamazaki |
| 4,153,855 A | 5/1979 | Feingold |
| 4,344,064 A | 8/1982 | Bitler et al. |
| 4,351,760 A | 9/1982 | Khanna et al. |
| 4,683,195 A | 7/1987 | Mullis et al. |
| 4,683,202 A | 7/1987 | Mullis |
| 4,707,237 A | 11/1987 | Lepp et al. |
| 4,711,955 A | 12/1987 | Ward et al. |
| 4,725,677 A | 2/1988 | Kosler et al. |
| 4,739,044 A | 4/1988 | Stabinsky |
| 4,757,141 A | 7/1988 | Fung et al. |
| 4,793,705 A | 12/1988 | Shera |
| 4,811,218 A | 3/1989 | Hunkapiller et al. |
| 4,863,849 A | 9/1989 | Melamede |
| 4,865,968 A | 9/1989 | Orgel et al. |
| 4,889,818 A | 12/1989 | Gelfand et al. |
| 4,942,124 A | 7/1990 | Church |
| 4,962,037 A | 10/1990 | Jett et al. |
| 4,971,903 A | 11/1990 | Hyman |
| 4,979,824 A | 12/1990 | Mathies et al. |
| 4,994,368 A | 2/1991 | Goodman et al. |
| 4,994,372 A | 2/1991 | Tabor et al. |
| 4,994,373 A | 2/1991 | Stavrianopoulos et al. |
| 5,085,562 A | 2/1992 | Van Lintel |
| 5,091,652 A | 2/1992 | Mathies et al. |
| 5,096,388 A | 3/1992 | Weinberg |
| 5,096,554 A | 3/1992 | Chin et al. |
| 5,108,892 A | 4/1992 | Burke et al. |
| 5,112,736 A | 5/1992 | Caldwell et al. |
| RE34,069 E | 9/1992 | Koster et al. |
| 5,143,854 A | 9/1992 | Pirrung et al. |
| 5,167,784 A | 12/1992 | Noolandi |
| 5,171,132 A | 12/1992 | Miyazaki et al. |
| 5,198,540 A | 3/1993 | Koster |
| 5,209,834 A | 5/1993 | Shera |
| 5,224,843 A | 7/1993 | Van Lintel |
| 5,242,796 A | 9/1993 | Prober et al. |
| 5,242,797 A | 9/1993 | Hirschfeld |
| 5,258,506 A | 11/1993 | Urdea et al. |
| 5,259,737 A | 11/1993 | Kamisuki et al. |
| 5,260,433 A | 11/1993 | Engelhardt et al. |
| 5,265,327 A | 11/1993 | Faris et al. |
| 5,267,152 A | 11/1993 | Yang et al. |
| 5,302,509 A | 4/1994 | Cheeseman |
| 5,304,487 A | 4/1994 | Wilding et al. |
| 5,306,403 A | 4/1994 | Vo-Dinh |
| 5,336,062 A | 8/1994 | Richter |
| 5,360,523 A | 11/1994 | Middendorf et al. |
| 5,375,979 A | 12/1994 | Trah |
| 5,376,252 A | 12/1994 | Ekstrom et al. |
| 5,403,709 A | 4/1995 | Agrawal et al. |
| 5,405,747 A | 4/1995 | Ieu et al. |
| 5,405,783 A | 4/1995 | Pirrung et al. |
| 5,409,811 A | 4/1995 | Tabor et al. |
| 5,424,186 A | 6/1995 | Fodor et al. |
| 5,436,149 A | 7/1995 | Barnes |
| 5,449,767 A | 9/1995 | Ward et al. |
| 5,476,928 A | 12/1995 | Ward et al. |
| 5,484,701 A | 1/1996 | Cocuzza et al. |
| 5,492,806 A | 2/1996 | Drmanac et al. |
| 5,514,256 A | 5/1996 | Douthart et al. |
| 5,518,900 A | 5/1996 | Nikiforov et al. |
| 5,525,464 A | 6/1996 | Drmanac et al. |
| 5,529,465 A | 6/1996 | Zengerle et al. |
| 5,534,125 A | 7/1996 | Middendorf et al. |
| 5,547,839 A | 8/1996 | Dower et al. |
| 5,547,859 A | 8/1996 | Goodman et al. |
| 5,556,790 A | 9/1996 | Pettit |
| 5,558,991 A | 9/1996 | Trainor |
| 5,599,695 A | 2/1997 | Pease et al. |
| 5,610,287 A | 3/1997 | Nikiforov et al. |
| 5,631,734 A | 5/1997 | Stern et al. |
| 5,632,957 A | 5/1997 | Heller et al. |
| 5,654,149 A | 8/1997 | Mendoza et al. |
| 5,659,171 A | 8/1997 | Young et al. |
| 5,670,346 A | 9/1997 | Reeve et al. |
| 5,674,716 A | 10/1997 | Tabor et al. |
| 5,675,155 A | 10/1997 | Pentoney, Jr. et al. |
| 5,688,648 A | 11/1997 | Mathies et al. |

(Continued)

FOREIGN PATENT DOCUMENTS

DE 10256898 A1 9/2004

(Continued)

OTHER PUBLICATIONS

Adam et al., "Individual genomes targeted in sequencing revolution", *Nature*, vol. 411, p. 402 (May 2001).

(Continued)

*Primary Examiner*—Patrick T Lewis
(74) *Attorney, Agent, or Firm*—Cooley Godward Kronish LLP

(57) ABSTRACT

The invention provides nucleotide analogs for use in sequencing nucleic acid molecules.

12 Claims, 2 Drawing Sheets

U.S. PATENT DOCUMENTS

| | | |
|---|---|---|
| 5,695,940 A | 12/1997 | Drmanac et al. |
| 5,705,018 A | 1/1998 | Hartley |
| 5,707,506 A | 1/1998 | Douthart et al. |
| 5,710,628 A | 1/1998 | Waterhouse et al. |
| 5,712,476 A | 1/1998 | Renfrew et al. |
| 5,733,729 A | 3/1998 | Lipshutz et al. |
| 5,741,640 A | 4/1998 | Fuller |
| 5,741,644 A | 4/1998 | Kambara et al. |
| 5,744,305 A | 4/1998 | Fodor et al. |
| 5,744,312 A | 4/1998 | Mamone et al. |
| 5,750,341 A | 5/1998 | Macevicz et al. |
| 5,753,788 A | 5/1998 | Fodor et al. |
| 5,755,943 A | 5/1998 | Middendorf et al. |
| 5,756,285 A | 5/1998 | Fuller |
| 5,759,014 A | 6/1998 | Van Lintel |
| 5,759,374 A | 6/1998 | Takahashi et al. |
| 5,762,876 A | 6/1998 | Lincoln et al. |
| 5,763,594 A | 6/1998 | Hiatt et al. |
| 5,776,767 A | 7/1998 | Stevens et al. |
| 5,776,782 A | 7/1998 | Tsuji |
| 5,789,168 A | 8/1998 | Leushner et al. |
| 5,795,722 A | 8/1998 | Lacroix et al. |
| 5,795,782 A | 8/1998 | Church et al. |
| 5,807,679 A | 9/1998 | Kamb |
| 5,808,045 A | 9/1998 | Hiatt et al. |
| 5,830,657 A | 11/1998 | Leushner et al. |
| 5,831,070 A | 11/1998 | Pease et al. |
| 5,832,165 A | 11/1998 | Reichert et al. |
| 5,834,758 A | 11/1998 | Trulson et al. |
| 5,836,750 A | 11/1998 | Cabuz |
| 5,837,832 A | 11/1998 | Chee et al. |
| 5,837,860 A | 11/1998 | Anderson et al. |
| 5,846,396 A | 12/1998 | Zanzucchi et al. |
| 5,846,727 A | 12/1998 | Soper et al. |
| 5,853,979 A | 12/1998 | Green et al. |
| 5,858,671 A | 1/1999 | Jones |
| 5,861,287 A | 1/1999 | Metzker et al. |
| 5,863,722 A | 1/1999 | Brenner |
| 5,872,244 A | 2/1999 | Hiatt et al. |
| 5,876,187 A | 3/1999 | Afromowitz |
| 5,876,934 A | 3/1999 | Duthie et al. |
| 5,882,904 A | 3/1999 | Riedl et al. |
| 5,885,813 A | 3/1999 | Davis et al. |
| 5,889,165 A | 3/1999 | Fodor et al. |
| 5,902,723 A | 5/1999 | Dower et al. |
| 5,908,755 A | 6/1999 | Kumar et al. |
| 5,916,747 A | 6/1999 | Gilchrist et al. |
| 5,922,591 A | 7/1999 | Anderson et al. |
| 5,922,608 A | 7/1999 | Farnsworth et al. |
| 5,928,906 A | 7/1999 | Koster et al. |
| 5,928,919 A | 7/1999 | Reha-Krantz et al. |
| 5,945,283 A | 8/1999 | Kwok et al. |
| 5,945,284 A | 8/1999 | Livak et al. |
| 5,945,312 A | 8/1999 | Goodman et al. |
| 5,945,325 A | 8/1999 | Arnold et al. |
| 5,948,614 A | 9/1999 | Chatterjee |
| 5,952,174 A | 9/1999 | Nikiforov et al. |
| 5,954,932 A | 9/1999 | Takahashi et al. |
| 5,958,703 A | 9/1999 | Dower et al. |
| 5,959,781 A | 9/1999 | Kintz et al. |
| 5,959,837 A | 9/1999 | Yu |
| 5,965,446 A | 10/1999 | Ishikawa |
| 5,968,740 A | 10/1999 | Fodor et al. |
| 5,974,164 A | 10/1999 | Chee |
| 5,976,338 A | 11/1999 | Fujita et al. |
| 5,981,186 A | 11/1999 | Gabe et al. |
| 5,981,956 A | 11/1999 | Stern |
| 5,994,058 A | 11/1999 | Senapathy |
| 5,994,085 A | 11/1999 | Cantor |
| 6,002,471 A | 12/1999 | Quake |
| 6,005,663 A | 12/1999 | Waterhouse et al. |
| 6,007,309 A | 12/1999 | Hartley |
| 6,015,714 A | 1/2000 | Baldarelli et al. |
| 6,017,702 A | 1/2000 | Lee et al. |
| 6,018,041 A | 1/2000 | Drmanac et al. |
| 6,020,457 A | 2/2000 | Klimash et al. |
| 6,024,925 A | 2/2000 | Little et al. |
| 6,025,136 A | 2/2000 | Drmanac |
| 6,028,190 A | 2/2000 | Mathies et al. |
| 6,030,782 A | 2/2000 | Anderson et al. |
| 6,043,080 A | 3/2000 | Lipshutz et al. |
| 6,046,005 A | 4/2000 | Ju et al. |
| 6,049,380 A | 4/2000 | Goodwin et al. |
| 6,051,380 A | 4/2000 | Sosnowski et al. |
| 6,066,454 A | 5/2000 | Lipshutz et al. |
| 6,071,394 A | 6/2000 | Cheng et al. |
| 6,077,664 A | 6/2000 | Slater et al. |
| 6,077,674 A | 6/2000 | Schleifer et al. |
| 6,087,095 A | 7/2000 | Rosenthal et al. |
| 6,087,099 A | 7/2000 | Gupte et al. |
| 6,094,274 A | 7/2000 | Yokoi |
| 6,107,032 A | 8/2000 | Kilger et al. |
| 6,107,044 A | 8/2000 | Nikiforov |
| 6,107,061 A | 8/2000 | Johnson |
| 6,132,580 A | 10/2000 | Mathies et al. |
| 6,133,436 A | 10/2000 | Koster et al. |
| 6,136,212 A | 10/2000 | Mastrangelo et al. |
| 6,136,962 A | 10/2000 | Shi et al. |
| 6,140,053 A | 10/2000 | Koster |
| 6,140,494 A | 10/2000 | Hamilton et al. |
| 6,141,096 A | 10/2000 | Stern et al. |
| 6,143,151 A | 11/2000 | Middendorf et al. |
| 6,147,205 A | 11/2000 | McGall et al. |
| 6,156,501 A | 12/2000 | McGall et al. |
| 6,165,694 A | 12/2000 | Liu |
| 6,177,249 B1 | 1/2001 | Kwok et al. |
| 6,197,506 B1 | 3/2001 | Fodor et al. |
| 6,197,595 B1 | 3/2001 | Anderson et al. |
| 6,207,381 B1 | 3/2001 | Larsson et al. |
| 6,207,960 B1 | 3/2001 | Stern |
| 6,210,896 B1 | 4/2001 | Chan |
| 6,214,246 B1 | 4/2001 | Craighead |
| 6,214,987 B1 | 4/2001 | Hiatt et al. |
| 6,221,592 B1 | 4/2001 | Schwartz et al. |
| 6,221,654 B1 | 4/2001 | Quake et al. |
| 6,225,052 B1 | 5/2001 | Batz et al. |
| 6,225,062 B1 | 5/2001 | Dunn et al. |
| 6,225,092 B1 | 5/2001 | Kilger et al. |
| 6,225,109 B1 | 5/2001 | Juncosa et al. |
| 6,225,567 B1 | 5/2001 | Kester |
| 6,225,625 B1 | 5/2001 | Pirrung et al. |
| 6,228,593 B1 | 5/2001 | Lipshutz et al. |
| 6,232,075 B1 | 5/2001 | Williams |
| 6,232,103 B1 | 5/2001 | Short |
| 6,235,465 B1 | 5/2001 | Kolberg et al. |
| 6,235,473 B1 | 5/2001 | Friedman et al. |
| 6,242,180 B1 | 6/2001 | Chee |
| 6,242,528 B1 | 6/2001 | Clark et al. |
| 6,245,506 B1 | 6/2001 | Laugharn, Jr. et al. |
| 6,245,507 B1 | 6/2001 | Bogdanov |
| 6,245,518 B1 | 6/2001 | Baier |
| 6,251,610 B1 | 6/2001 | Gupte et al. |
| 6,255,083 B1 | 7/2001 | Williams |
| 6,255,475 B1 | 7/2001 | Kwiatkowski |
| 6,258,533 B1 | 7/2001 | Jones |
| 6,261,775 B1 | 7/2001 | Bastian et al. |
| 6,261,776 B1 | 7/2001 | Pirrung et al. |
| 6,261,848 B1 | 7/2001 | Anderson et al. |
| 6,262,838 B1 | 7/2001 | Montagu |
| 6,263,286 B1 | 7/2001 | Gilmanshin et al. |
| 6,268,152 B1 | 7/2001 | Fodor et al. |
| 6,268,219 B1 | 7/2001 | Mcbride et al. |
| 6,269,846 B1 | 8/2001 | Overbeck et al. |
| 6,270,644 B1 | 8/2001 | Mathies et al. |

| Patent No. | Date | Inventor(s) |
|---|---|---|
| 6,270,961 B1 | 8/2001 | Drmanac |
| 6,274,320 B1 | 8/2001 | Rothberg et al. |
| 6,274,351 B1 | 8/2001 | Peponnet |
| 6,277,604 B1 | 8/2001 | Peponnet |
| 6,280,954 B1 | 8/2001 | Ulfendahl |
| 6,284,460 B1 | 9/2001 | Fodor et al. |
| 6,287,821 B1 | 9/2001 | Shi et al. |
| 6,294,336 B1 | 9/2001 | Boyce-Jacino et al. |
| 6,294,337 B1 | 9/2001 | Hayashizaki |
| 6,306,607 B2 | 10/2001 | Williams |
| 6,309,601 B1 | 10/2001 | Juncosa et al. |
| 6,309,701 B1 | 10/2001 | Barbera-Guillem |
| 6,309,824 B1 | 10/2001 | Drmanac |
| 6,309,836 B1 | 10/2001 | Kwiatowski |
| 6,309,886 B1 | 10/2001 | Ambrose et al. |
| 6,310,189 B1 | 10/2001 | Fodor et al. |
| 6,312,893 B1 | 11/2001 | Van Ness et al. |
| 6,316,191 B1 | 11/2001 | Drmanac et al. |
| 6,322,968 B1 | 11/2001 | Head et al. |
| 6,331,439 B1 | 12/2001 | Cherukuri et al. |
| 6,333,183 B1 | 12/2001 | Evans et al. |
| 6,335,824 B1 | 1/2002 | Overbeck |
| 6,337,185 B1 | 1/2002 | Asp et al. |
| 6,337,188 B1 | 1/2002 | Head et al. |
| 6,342,326 B1 | 1/2002 | Milton |
| 6,344,325 B1 | 2/2002 | Quake et al. |
| 6,346,379 B1 | 2/2002 | Gelfand et al. |
| 6,346,413 B1 | 2/2002 | Fodor et al. |
| 6,355,420 B1 | 3/2002 | Chao |
| 6,355,432 B1 | 3/2002 | Fodor et al. |
| 6,361,671 B1 | 3/2002 | Mathies et al. |
| 6,361,937 B1 | 3/2002 | Stryer |
| 6,368,562 B1 | 4/2002 | Yao |
| 6,368,699 B1 | 4/2002 | Gilbert et al. |
| 6,383,749 B2 | 5/2002 | Bochkariov et al. |
| 6,387,626 B1 | 5/2002 | Shi et al. |
| 6,395,232 B1 | 5/2002 | McBride |
| 6,395,559 B1 | 5/2002 | Swenson |
| 6,397,150 B1 | 5/2002 | Izmailov |
| 6,399,364 B1 | 6/2002 | Reeve et al. |
| 6,401,267 B1 | 6/2002 | Drmanac |
| 6,403,311 B1 | 6/2002 | Chao |
| 6,403,315 B1 | 6/2002 | Drmanac |
| 6,403,317 B1 | 6/2002 | Anderson |
| 6,403,320 B1 | 6/2002 | Read et al. |
| 6,403,957 B1 | 6/2002 | Fodor et al. |
| 6,404,907 B1 | 6/2002 | Gilchrist et al. |
| 6,406,893 B1 | 6/2002 | Knapp et al. |
| 6,407,858 B1 | 6/2002 | Montagu |
| 6,408,878 B2 | 6/2002 | Unger et al. |
| 6,416,952 B1 | 7/2002 | Pirrung et al. |
| 6,420,169 B1 | 7/2002 | Read et al. |
| 6,423,273 B1 | 7/2002 | O'Mara |
| 6,432,634 B1 | 8/2002 | Digby et al. |
| 6,436,641 B1 | 8/2002 | Izmailov |
| 6,436,646 B1 | 8/2002 | Nikiforov |
| 6,440,664 B1 | 8/2002 | Digby et al. |
| 6,440,722 B1 | 8/2002 | Knapp et al. |
| 6,444,106 B1 | 9/2002 | Mcbride et al. |
| 6,444,173 B1 | 9/2002 | Sjursen et al. |
| 6,444,424 B1 | 9/2002 | Chatterjee et al. |
| 6,444,461 B1 | 9/2002 | Knapp et al. |
| 6,447,724 B1 | 9/2002 | Jensen et al. |
| 6,448,090 B1 | 9/2002 | McBride |
| 6,451,536 B1 | 9/2002 | Fodor et al. |
| 6,479,267 B1 | 11/2002 | Davis et al. |
| 6,485,690 B1 | 11/2002 | Pfost et al. |
| 6,485,909 B1 | 11/2002 | Hong et al. |
| 6,485,944 B1 | 11/2002 | Church et al. |
| 6,495,363 B2 | 12/2002 | Bogdanov |
| 6,506,560 B1 | 1/2003 | Hughes et al. |
| 6,511,803 B1 | 1/2003 | Church et al. |
| 6,514,706 B1 | 2/2003 | Von Kalle et al. |
| 6,521,428 B1 | 2/2003 | Senapathy |
| 6,524,829 B1 | 2/2003 | Seeger |
| 6,528,258 B1 | 3/2003 | Russell |
| 6,528,288 B2 | 3/2003 | Senapathy |
| 6,537,755 B1 | 3/2003 | Drmanac |
| 6,537,757 B1 | 3/2003 | Langmore et al. |
| 6,546,340 B2 | 4/2003 | Lipshutz et al. |
| 6,551,784 B2 | 4/2003 | Fodor et al. |
| 6,551,817 B2 | 4/2003 | Besemer et al. |
| 6,554,987 B1 | 4/2003 | Gilchrist et al. |
| 6,555,349 B1 | 4/2003 | O'Donnell |
| 6,558,945 B1 | 5/2003 | Kao |
| 6,562,566 B1 | 5/2003 | Hoheisel |
| 6,566,059 B1 | 5/2003 | Stanton, Jr. et al. |
| 6,566,515 B1 | 5/2003 | McGall et al. |
| 6,573,047 B1 | 6/2003 | Hung et al. |
| 6,573,374 B1 | 6/2003 | Muehleger et al. |
| 6,576,424 B2 | 6/2003 | Fodor et al. |
| 6,576,425 B2 | 6/2003 | McGall et al. |
| 6,579,704 B2 | 6/2003 | Short |
| 6,582,923 B2 | 6/2003 | Stanton, Jr. et al. |
| 6,585,939 B1 | 7/2003 | Dapprich |
| 6,607,888 B2 | 8/2003 | Schwartz et al. |
| 6,610,482 B1 | 8/2003 | Fodor et al. |
| 6,613,513 B1 | 9/2003 | Kopf-Sill et al. |
| 6,623,928 B2 | 9/2003 | Van Ness et al. |
| 6,627,748 B1 | 9/2003 | Ju et al. |
| 6,632,655 B1 | 10/2003 | Mehta et al. |
| 6,642,001 B1 | 11/2003 | Bolk et al. |
| 6,664,079 B2 | 12/2003 | Ju et al. |
| 6,719,868 B1 | 4/2004 | Schueller et al. |
| 6,750,018 B2 | 6/2004 | Kambara et al. |
| 6,762,048 B2 | 7/2004 | Williams |
| 6,780,591 B2 | 8/2004 | Williams et al. |
| 6,783,938 B2 | 8/2004 | Nygren et al. |
| 6,787,308 B2 | 9/2004 | Balasubramanian et al. |
| 6,818,395 B1 | 11/2004 | Quake et al. |
| 6,908,736 B1 | 6/2005 | Densham |
| 6,911,345 B2 | 6/2005 | Quake et al. |
| 7,057,026 B2 * | 6/2006 | Barnes et al. ............... 536/23.1 |
| 2001/0024790 A1 | 9/2001 | Kambara et al. |
| 2001/0044531 A1 | 11/2001 | McGall et al. |
| 2001/0046681 A1 | 11/2001 | Senapathy |
| 2002/0009744 A1 | 1/2002 | Bogdanov |
| 2002/0012910 A1 | 1/2002 | Weiss et al. |
| 2002/0015961 A1 | 2/2002 | Kwiatkowski |
| 2002/0025529 A1 | 2/2002 | Quake et al. |
| 2002/0032320 A1 | 3/2002 | Burgess et al. |
| 2002/0034792 A1 | 3/2002 | Kilger et al. |
| 2002/0039738 A1 | 4/2002 | Williams et al. |
| 2002/0042112 A1 | 4/2002 | Koster et al. |
| 2002/0045182 A1 | 4/2002 | Singh et al. |
| 2002/0051992 A1 | 5/2002 | Bridgham et al. |
| 2002/0053532 A1 | 5/2002 | Quake et al. |
| 2002/0061529 A1 | 5/2002 | Bridgham et al. |
| 2002/0072055 A1 | 6/2002 | Jones |
| 2002/0086318 A1 | 7/2002 | Manalis et al. |
| 2002/0102586 A1 | 8/2002 | Ju et al. |
| 2002/0102595 A1 | 8/2002 | Davis |
| 2002/0106673 A1 | 8/2002 | Drmanac et al. |
| 2002/0115076 A1 | 8/2002 | Williams |
| 2002/0115092 A1 | 8/2002 | Rebek, Jr. |
| 2002/0119484 A1 | 8/2002 | Weidenhammer et al. |
| 2002/0123046 A1 | 9/2002 | Smith et al. |
| 2002/0137046 A1 | 9/2002 | Koster |
| 2002/0137052 A1 | 9/2002 | Bridgham et al. |
| 2002/0137062 A1 | 9/2002 | Williams et al. |
| 2002/0138205 A1 | 9/2002 | Miller et al. |
| 2002/0142329 A1 | 10/2002 | Matray et al. |
| 2002/0142333 A1 | 10/2002 | Gelfand et al. |
| 2002/0146704 A1 | 10/2002 | Head et al. |
| 2002/0146726 A1 | 10/2002 | Matray et al. |
| 2002/0150903 A1 | 10/2002 | Koster |

| | | | | | | |
|---|---|---|---|---|---|---|
| 2002/0150938 | A1 | 10/2002 | Kneipp et al. | EP | 0779436 A2 | 6/1997 |
| 2002/0164629 | A1 | 11/2002 | Quake et al. | EP | 0845603 A1 | 6/1998 |
| 2002/0168642 | A1 | 11/2002 | Drukier | EP | 0932700 B1 | 8/1999 |
| 2002/0168678 | A1 | 11/2002 | Williams et al. | EP | 0946752 B1 | 10/1999 |
| 2002/0172948 | A1 | 11/2002 | Perlin | EP | 0955085 A2 | 11/1999 |
| 2002/0177129 | A1 | 11/2002 | Paabo et al. | EP | 0999055 A2 | 5/2000 |
| 2002/0182601 | A1 | 12/2002 | Sampson et al. | EP | 0706004 B1 | 8/2003 |
| 2002/0192661 | A1 | 12/2002 | Paabo et al. | GB | 2155152 A | 9/1985 |
| 2002/0192662 | A1 | 12/2002 | Boyce-Jacino et al. | GB | 2308460 A | 6/1997 |
| 2002/0192691 | A1 | 12/2002 | Drmanac | GB | 2400518 A | 10/2004 |
| 2002/0197618 | A1 | 12/2002 | Sampson | JP | 63-241356 * | 10/1988 |
| 2003/0003272 | A1 | 1/2003 | Laguitton | SE | 9500589 | 2/1995 |
| 2003/0003498 | A1 | 1/2003 | Digby et al. | WO | 89/03432 A1 | 4/1989 |
| 2003/0008285 | A1 | 1/2003 | Fischer | WO | 89/09283 A1 | 10/1989 |
| 2003/0008413 | A1 | 1/2003 | Kim et al. | WO | 90/13666 A1 | 11/1990 |
| 2003/0017461 | A1 | 1/2003 | Singh et al. | WO | 90/15070 A1 | 12/1990 |
| 2003/0022207 | A1 | 1/2003 | Balasubramanian et al. | WO | 91/06678 A1 | 5/1991 |
| 2003/0027140 | A1 | 2/2003 | Ju et al. | WO | 92/10092 A1 | 6/1992 |
| 2003/0036080 | A1 | 2/2003 | Jensen et al. | WO | 92/10587 A1 | 6/1992 |
| 2003/0044778 | A1 | 3/2003 | Goelet et al. | WO | 93/05183 A1 | 3/1993 |
| 2003/0044779 | A1 | 3/2003 | Goelet et al. | WO | 93/06121 A1 | 4/1993 |
| 2003/0044781 | A1 | 3/2003 | Korlach et al. | WO | 93/21340 A1 | 10/1993 |
| 2003/0044816 | A1 | 3/2003 | Denison et al. | WO | 95/12608 A1 | 5/1995 |
| 2003/0054181 | A1 | 3/2003 | Swerdlow et al. | WO | 95/27080 A1 | 10/1995 |
| 2003/0054361 | A1 | 3/2003 | Heller | WO | 96/04547 A1 | 2/1996 |
| 2003/0058440 | A1 | 3/2003 | Scott et al. | WO | 96/12014 A1 | 4/1996 |
| 2003/0058799 | A1 | 3/2003 | Yamakawa et al. | WO | 96/12039 A1 | 4/1996 |
| 2003/0059778 | A1 | 3/2003 | Berlin et al. | WO | 96/27025 A1 | 9/1996 |
| 2003/0060431 | A1 | 3/2003 | Simmonds et al. | WO | 97/02488 A1 | 1/1997 |
| 2003/0064366 | A1 | 4/2003 | Hardin et al. | WO | 97/22076 A1 | 6/1997 |
| 2003/0064398 | A1 | 4/2003 | Barnes | WO | 97/23650 A2 | 6/1997 |
| 2003/0064483 | A1 | 4/2003 | Shaw et al. | WO | 97/37041 A2 | 10/1997 |
| 2003/0087237 | A1 | 5/2003 | Hong et al. | WO | 97/39150 A1 | 10/1997 |
| 2003/0087300 | A1 | 5/2003 | Knapp et al. | WO | 97/40184 A1 | 10/1997 |
| 2003/0092005 | A1 | 5/2003 | Levene et al. | WO | 97/41258 A1 | 11/1997 |
| 2003/0092007 | A1 | 5/2003 | Gibbs et al. | WO | 97/41259 A1 | 11/1997 |
| 2003/0096258 | A1 | 5/2003 | Fu et al. | WO | 97/42348 A1 | 11/1997 |
| 2003/0100006 | A1 | 5/2003 | Senapathy | WO | 98/00708 A1 | 1/1998 |
| 2003/0104437 | A1 | 6/2003 | Barnes et al. | WO | 98/02575 A1 | 1/1998 |
| 2003/0104466 | A1 | 6/2003 | Knapp et al. | WO | 98/03684 A1 | 1/1998 |
| 2003/0108867 | A1 | 6/2003 | Chee et al. | WO | 98/07069 A1 | 2/1998 |
| 2003/0138809 | A1 | 7/2003 | Williams et al. | WO | 98/13523 A1 | 4/1998 |
| 2003/0148344 | A1 | 8/2003 | Rothberg et al. | WO | 98/08978 A1 | 5/1998 |
| 2003/0162213 | A1 | 8/2003 | Fuller et al. | WO | 98/20019 A1 | 5/1998 |
| 2003/0186227 | A1 | 10/2003 | Balasubramanian et al. | WO | 98/20020 A2 | 5/1998 |
| 2003/0186255 | A1 | 10/2003 | Williams et al. | WO | 98/20166 A2 | 5/1998 |
| 2003/0190627 | A1 | 10/2003 | Zhao et al. | WO | 98/21361 A1 | 5/1998 |
| 2003/0190647 | A1 | 10/2003 | Odera | WO | 98/27228 A1 | 6/1998 |
| 2003/0190663 | A1 | 10/2003 | Yang et al. | WO | 98/28440 A1 | 7/1998 |
| 2003/0194722 | A1 | 10/2003 | Odedra et al. | WO | 98/33939 A1 | 8/1998 |
| 2003/0194740 | A1 | 10/2003 | Williams | WO | 98/40520 A1 | 9/1998 |
| 2003/0215862 | A1 | 11/2003 | Wallace et al. | WO | 98/41650 A2 | 9/1998 |
| 2004/0009487 | A1 | 1/2004 | Kadushin et al. | WO | 98/41657 A1 | 9/1998 |
| 2004/0014096 | A1 | 1/2004 | Anderson et al. | WO | 98/44152 A1 | 10/1998 |
| 2004/0029115 | A9 | 2/2004 | Dower et al. | WO | 98/45481 A1 | 10/1998 |
| 2004/0038206 | A1 | 2/2004 | Zhang et al. | WO | 98/53300 A2 | 11/1998 |
| 2004/0054162 | A1 | 3/2004 | Hanna | WO | 98/54669 A1 | 12/1998 |
| 2004/0106110 | A1 | 6/2004 | Balasubramanian et al. | WO | 98/55593 A1 | 12/1998 |
| 2004/0110162 | A1 | 6/2004 | Lapidus et al. | WO | 99/01768 A1 | 1/1999 |
| 2004/0126770 | A1 | 7/2004 | Kumar et al. | WO | 99/05221 A1 | 2/1999 |
| 2005/0014175 | A1 | 1/2005 | Quake et al. | WO | 99/05315 A2 | 2/1999 |
| 2005/0100932 | A1 | 5/2005 | Lapidus et al. | WO | 99/06422 A2 | 2/1999 |
| 2005/0147992 | A1 | 7/2005 | Quake et al. | WO | 99/13109 A1 | 3/1999 |
| 2005/0170367 | A1 | 8/2005 | Quake et al. | WO | 99/13110 A1 | 3/1999 |
| 2005/0239085 | A1 | 10/2005 | Buzby et al. | WO | 99/09616 A1 | 4/1999 |
| | | | | WO | 99/17093 A1 | 4/1999 |
| | | FOREIGN PATENT DOCUMENTS | | WO | 99/19516 A1 | 4/1999 |
| | | | | WO | 99/24797 A1 | 5/1999 |
| EP | 0223618 A2 | 5/1987 | | WO | 99/27137 A1 | 6/1999 |
| EP | 0412883 A1 | 2/1991 | | WO | 99/31278 A1 | 6/1999 |
| EP | 0579997 A1 | 1/1994 | | WO | 99/37810 A1 | 7/1999 |
| EP | 0703364 A1 | 3/1996 | | WO | 99/39001 A2 | 8/1999 |
| EP | 0706004 A2 | 4/1996 | | WO | 99/40105 A2 | 8/1999 |

| | | |
|---|---|---|
| WO | 99/40223 A1 | 8/1999 |
| WO | 99/41410 A1 | 8/1999 |
| WO | 00/30591 A1 | 9/1999 |
| WO | 99/44045 A1 | 9/1999 |
| WO | 99/45153 A2 | 9/1999 |
| WO | 99/47539 A1 | 9/1999 |
| WO | 99/47706 A1 | 9/1999 |
| WO | 99/53423 A1 | 10/1999 |
| WO | 99/57321 A1 | 11/1999 |
| WO | 99/61888 A2 | 12/1999 |
| WO | 99/64437 A1 | 12/1999 |
| WO | 99/64840 A1 | 12/1999 |
| WO | 99/65938 A2 | 12/1999 |
| WO | 99/66076 A1 | 12/1999 |
| WO | 99/66313 A1 | 12/1999 |
| WO | 00/00637 A2 | 1/2000 |
| WO | 00/06770 A1 | 2/2000 |
| WO | 00/09753 A1 | 2/2000 |
| WO | 00/11223 A1 | 3/2000 |
| WO | 00/17397 A1 | 3/2000 |
| WO | 00/26935 A2 | 5/2000 |
| WO | 00/34523 A1 | 6/2000 |
| WO | 00/37680 A1 | 6/2000 |
| WO | 00/40750 A1 | 7/2000 |
| WO | 00/40758 A2 | 7/2000 |
| WO | 00/42223 A1 | 7/2000 |
| WO | 00/43540 A1 | 7/2000 |
| WO | 00/43752 A1 | 7/2000 |
| WO | 00/50642 A1 | 8/2000 |
| WO | 00/53805 A1 | 9/2000 |
| WO | 00/53812 A2 | 9/2000 |
| WO | 00/56937 A2 | 9/2000 |
| WO | 00/58507 A1 | 10/2000 |
| WO | 00/58516 A2 | 10/2000 |
| WO | 00/68410 A1 | 11/2000 |
| WO | 00/70073 A1 | 11/2000 |
| WO | 00/71755 A2 | 11/2000 |
| WO | 00/79007 A1 | 12/2000 |
| WO | 01/001025 A2 | 1/2001 |
| WO | 01/16375 A2 | 3/2001 |
| WO | 01/23610 A2 | 4/2001 |
| WO | 01/24937 A2 | 4/2001 |
| WO | 01/25480 A2 | 4/2001 |
| WO | 01/31055 A2 | 5/2001 |
| WO | 01/32930 A1 | 5/2001 |
| WO | 01/38574 A1 | 5/2001 |
| WO | 01/48184 A2 | 5/2001 |
| WO | 01/42496 A2 | 6/2001 |
| WO | 01/57248 A2 | 8/2001 |
| WO | 01/57249 A1 | 8/2001 |
| WO | 01/61044 A1 | 8/2001 |
| WO | 01/64838 A2 | 9/2001 |
| WO | 01/75154 A2 | 10/2001 |
| WO | 01/79536 A1 | 10/2001 |
| WO | 01/85991 A2 | 11/2001 |
| WO | 01/92284 A1 | 12/2001 |
| WO | 01/96607 A2 | 12/2001 |
| WO | 02/00343 A2 | 1/2002 |
| WO | 02/02584 A1 | 1/2002 |
| WO | 02/02795 A2 | 1/2002 |
| WO | 02/02813 A2 | 1/2002 |
| WO | 02/03305 A2 | 1/2002 |
| WO | 02/04680 A2 | 1/2002 |
| WO | 02/20836 A2 | 3/2002 |
| WO | 02/20837 A2 | 3/2002 |
| WO | 02/27032 A1 | 4/2002 |
| WO | 02/29106 A2 | 4/2002 |
| WO | 02/030486 A3 | 4/2002 |
| WO | 02/35441 A2 | 5/2002 |
| WO | 02/36832 A2 | 5/2002 |
| WO | 02/44414 A2 | 6/2002 |
| WO | 02/061126 A2 | 8/2002 |
| WO | 02/061127 A2 | 8/2002 |
| WO | 02/072779 A2 | 9/2002 |
| WO | 02/072892 A1 | 9/2002 |
| WO | 02/077694 A1 | 10/2002 |
| WO | 02/079519 A1 | 10/2002 |
| WO | 02/088381 A2 | 11/2002 |
| WO | 02/088382 A2 | 11/2002 |
| WO | 02/097113 A2 | 12/2002 |
| WO | 02/099398 A1 | 12/2002 |
| WO | 03/002767 A1 | 1/2003 |
| WO | 03/016565 A2 | 2/2003 |
| WO | 03/020895 A2 | 3/2003 |
| WO | 03/020968 A2 | 3/2003 |
| WO | 03/021010 A2 | 3/2003 |
| WO | 03/031947 A2 | 4/2003 |
| WO | 03/044678 A1 | 5/2003 |
| WO | 03/048178 A2 | 6/2003 |
| WO | 03/048991 A2 | 6/2003 |
| WO | 03/062897 A1 | 7/2003 |
| WO | 03/106642 A2 | 12/2003 |
| WO | 2004/061119 A2 | 7/2004 |
| WO | 2004/074503 A2 | 9/2004 |
| WO | 2005/047523 A2 | 5/2005 |
| WO | 2005/080605 A2 | 9/2005 |

OTHER PUBLICATIONS

Agrawal, S. et al., "Site Specific Functionalization of Oligodeoxynucleotides for Non-Radioactive Labelling", *Tetrahedron Letters*, vol. 31, No. 11, pp. 1543-1546 (1990).

Ambrose, W. et al., "Single Molecule Detection With Total Internal Reflection Excitation: Comparing Signal-to-Background and Total Signals in Different Geometries", *Cytometry*, vol. 36, pp. 224-231 (1999).

Amit, B. et al., "Photosensitive Protecting Groups of Amino Sugars and Their Use in Glycoside Synthesis . . . Derivatives", *J. Org. Chem.*, 39(2):192-6 (1974).

Arndt-Jovin, D. et al., "Immunofluorescence Localization of Z-DNA in Chromosomes: Quantitation by Scanning Microphotometry and Computer-assisted Image Analysis", 1. *The Journal of Cell Biology*, vol. 101, pp. 1422-1433, (Oct. 1985).

Augustin, M.A., W. Ankenbauer, and B. Angerer, "Progress towards single-molecule sequencing: enzymatic synthesis of nucleotide-specifically labeled DNA." *Journal of Biotechnology*, 8(13): 289-301 (2001).

Axelrod, D., "Cell-Substrate Contacts Illuminated by Total Internal Reflection Fluorescence", 1. *The Journal of Cell Biology*, vol. 89, pp. 141-145, (Apr. 1981).

Axelrod, D. et al., "Total internal reflection fluorescent microscopy", *J Microscopy*, vol. 129, pp. 19-28, (1983).

Bai, X., et al., "Photocleavage of a 2-nitrobenzyl linker bridging a fluorophore to the 5' end of DNA." Proc Natl Acad Sci USA, 2003, vol. 100(2). p. 409-13.

Basche, T. et al., "Single Molecule Optical Detection, Imaging and Spectroscopy", Chs. 2 and 3, Weinheim:VCM, Germany (1997).

Beaucage, S. et al., "Advances in the Synthesis of Oligonucleotides by the Phosphoramidite Approach" *Tetrahedron*, 48:2223-2311 (1992).

Beese, L. et al., "Structure of DNA Polymerase I Klenow Fragment Bound to Duplex DNA", *Science*, 260:352-355 (1993).

Bennett. al., "Solexa Sequencing chemistry can be applied to different platforms which will have common elements in detection and data processing", *Pharmacogenomics* 5(4), pp. 433-438, (2004).

Biesalski et al., "Preparation and Characterization of a Polyelectrolyte Monolayer Covalently Attached to a Planar Solid Surface", *Macromolecules* 111, 32, 2309-2316. Article was published on the web Mar. 10, 1999.

Black, D.L., "Protein diversity from alternating splicing: A challenge for bioinformatics and post genome biology", *Cell*, 2000. 103(3): p. 367-370.

Blattner, F.R., et al., "The Complete genome sequence of *Escherichia coli* K-12.", *Science*, 277: 1453-74 (1997).

Boles et. al., "High-Resolution Mapping of Carcinogen Binding Sites on DNA", *Biochemistry*, 1986, 25, 3039-3043.

Brakmann, S. and P. Nieckchen, "The large fragment of *Escherichia coli* DNA polymerase I can synthesize DNA exclusively from fluorescently labeled nucleotides." *Chembiochem*, 2(10): 773-777 (2001).

Brakmann et. al, "Optimal Enzymes for Single-Molecule Sequencing", *Current Pharmaceutical Biotechnology*, 5, pp. 119-126 (2004).

Braslavsky, I. et al., "Sequence information can be obtained from single DNA molecules", *PNAS*, vol. 100, No. 7, pp. 3960-3964 (Apr. 2003).

Braslavsky, I. et al., "Objective-type dark-field illumination for scattering from microbeads", *Applied Optics*, vol. 40, No. 31, pp. 5650-5657, (Nov. 2001).

Braslavsky, I. et al., "Single Molecule Measurements of DNA Polymerase Activity: A Step Towards Single Molecule Sequencing", *Biophys. I. Abstracts*, p. 507A (2002).

Brechtel, R. et al., "Control of the electro osmotic flow by metal-salt-containing buffers", *J. Chromatoraphy A*, vol. 716, pp. 97-105, (1995).

Bridgman, A. et al., "An improved method for the synthesis of mercurated dUTP. Enzymatic synthesis of Hg-Iabelled DNA of high molecular weight suitable for use in an image based DNA sequencing strategy", *DNA Seq.*, vol. 6, No. 4, pp. 199-209 (1996).

Bruggert, J. et al., "Microfabricated tools for nanoscience", *J. Micromech. Microeng.*, 3, pp. 161-167 (1993).

Bryzek, J. etal., "Micromachines on the march", *IEEE Spectrum*, vol. 31, No. 5, pp. 20-31, (1994).

Buchaillot, L. et al., "Silicon Nitride Thin Films Young's Modulus Determination by an Optical Non Destructive Method", *Jpn. J. Appl. Phys.*, vol. 36, pp. L794-L797, (Jun. 1997).

Burghardt, T. et al., "Total Internal Reflection Fluorescence Study of Energy Tansfer in Surface-Adsorbed and Dissolved Bovine Serum Albumin", *Biochemistry*, vol. 22, pp. 979-985 (1983).

Burghardt, et al., "Total Internal Reflection/Fluorescence Photobleaching Recovery Study of Serum Albumin Adsorption Dynamics", *Biophys. Journal*, vol. 33, pp. 455-468 (Mar. 1981).

Butler, D. et al., "Draft data leave geneticists with a mountain still to climb", *Nature*, vol. 405, Issue 6782, pp. 984-985 (May 2000).

Canard, B., B. Cardona, .and R.S. Sarfati, "Catalytic editing properties of DNA polymerases," *Proc Natl Acad Sci USA*, 92(24): p. 10859-63 (1995).

Canard, et al., "DNA polymerase fluorescent substratics with reversible 3'-tags", *Gene*, 148(1): 1-6 (1994).

Cheng et al., "High-speed DNA sequence analysis," *Prog. in Biochem. and Biophys.*, vol. 22, pp. 223-227 (1995).

Chicurel, M., "Faster, better, cheaper genotyping", *Nature*, vol. 412, Issue 6847, pp. 580-582, (Aug. 2001).

Chidgeavadze et al., 2',3'-Dideoxy-3' aminonucleoside 5'-triphosphates are the terminators of DNA synthesis catalyzed by DNA polymerases, *Nuc. Acids Res.*, 12(3):1671-1686 (1984).

Chidgeavadze, Z. et al., "3'-Fluro-2',3'-dideoxyribonucleoside 5'-triphosphates: terminators of DNA synthesis", *FEBS Letters*, 183(2):275-278 (1985).

Chiu, D. et al., "Patterned deposition of cells and proteins onto surfaces by using three-dimensional microfluidic systems," *PNAS*, vol. 97, No. 6, pp. 2408-2413 (2000).

Chou et al., "A microfabricated device for sizing and sorting DNA molecules", Applied Sciences, Biophysics: Proc. Natl. Acad. Sci. USA 96, pp. 11-13 (1999).

Chou et al., "A Microfabricated Rotary Pump", *Biomedical Microdevices*. vol. 3: p. 323-330 (2001).

Close, D. et al., "Ultraviolet Photobleaching of Free Radicals Created in y-Irradiated Amino Acids", *Radiation Research*, vol. 53, pp. 349-357 (1973).

Cooper, J. et al., "Analysis of Fluorescence Energy Transfer in Duplex and Branched DNA Molecules", *Biochemistry*, vol. 29, pp. 9261-9268 (1990).

Crocker, J.C. and D.G. Grier, "Methods of digital video microscopy for colloidal studies." *Journal of Colloid and Interface Science*, 179(1): p. 298-310 (1996).

Dapprich, J., "Single-molecule DNA digestion by lambda-exonuclease." *Cytometry*, 36(3): p. 163-168 (1999).

Debenham, J.S., et al., "Two New Orthogonal Amine-Protecting Groups that can be Cleaved under Mild or Neutral Conditions." *Journal of the American Chemical Society*, 117(11): p. 3302-3 (1995).

Decher, G. et al., "Buildup of ultrathin multiplayer films by a self-assembly process: III. Consecutively alternating absorption of anionic and cationic polyelectrolytes on charged surfaces", *Thin Solid Films*, 210-831-835 (1992).

Decher G.;et al., "Fuzzy nanoassemblies : Toward layered polymeric multicomposites." *Science*, 277(5330): p. 1232-1237 (1997).

Delamarche, E. et al., "Patterned Delivery of Immunoglobulins to Surfaces Using Microfluidic Networks", *Science* 276:779-781 (1997).

Dickson et al., "Simultaneous Imaging of Individual Molecules aligned both parallel and perpendicular to the optic axis", *The American Physical Society*, vol. 81, No. 24, pp. 5322-5325 (1998).

Doktycz, M. et al., "Genoscensors and Model Hybridization Studies", *Automation Technologies for Genome Characterization*, Ch. 10 T. Beugelsdijk (Ed), John Wiley & Sons, Inc., pp. 205-225 (1997).

Doublie, S. et al., "Crystal structure of a bacteriophage T7 DNA replication complex at 2.2 A resolution", *Nature*, vol. 391, pp. 251-258 (Jan. 1998).

Driscoll et al., "Atomic-Scale Imaging of DNA Using Scanning Tunneling Microscopy." *Nature*, 346(6281): p. 294-296 (1990).

Drmanac, R. et al., "Sequencing by hybridization: Towards an automated sequencing of one million M13 clones arrayed on membranes", *Electrophoresis*, 13:566-573 (1992).

Duffy et al., "Patterning Electroluminescence Materials with Feature Sizes as Small as 5 um Using Elastomeric Membranes as Masks for Dry Lift-Off," *Advanced Materials* vol. 11, No. 7, pp. 546-552 (1999).

Duffy et al., "Rapid prototyping of microfluidic switches in poly(dimethyl siloxane) and their acuation by electroosmotic flow," *J. Micromech. Microeng.*, vol. 9, pp. 211-217 (1999).

Duffy et al., "Rapid Prototyping of Microfluidic Systems in Poly(dimethylsiloxane)", *Analytical Chemistry*, vol. 70, No. 23, pp. 4974-4984 (1998).

Effenhauser et al., "Integrated capillary electrophoresis on Flexible silicone microdevices: Analysis of DNA restriction fragments and detection of single DNA molecules on microchips," *Anal. Chem.*, vol. 69, pp. 3451-3457 (1997).

Effenhauser et al., "Integrated chip-based capillary electrophoresis," *Electrophoresis*, vol. 18, pp. 2203-2213 (1997).

Eigen, M. et al., "Sorting single molecules: Application to diagnostics and evolutionary biotechnology", *PNAS*, vol. 91, pp. 5740-5747, (Jun. 1994).

Evangelista, R.A., et al. "Characterization of fluorescent nucleoside triphosphates by capillary electrophoresis with laser-induced fluorescence detection: action of alkaline phosphatase and DNA polymerase." *Analytical Biochemistry*, 235(1): p. 89-97 (1996).

Fahrenberg et al., "A microvalve system fabricated by thermoplastic molding," J. Micromech. Microeng., vol. 5, pp. 169-171(1995).

Ferguson, et al., "A fiber-optic DNA biosensor microarray for the analysis of gene expression," *Nature Biotechnology*, vol. 14, pp. 1681-1684 (1996).

Forster, T., "Delocalized Excitation and Excitation Transfer", Modern Quantum Chem., *Istanbul Lectures*, Part TII, pp. 93-137, Academic Press, New York (1965).

Fritz, I. et al., "Electronic detection of DNA by its intrinsic molecular charge", *PNAS*, vol. 99, No. 22, pp. 14142-14146 (Oct. 2002).

Fu et al., "A microfabricated fluorescence-activated cell sorter," *Nature Biotechnology*, vol. 17, pp. 1109-1111 (1999).

Fu e al., "An integrated microfabricated cell sorter", *Analytical Chemistry*, 74(11): pp. 2451-2457 (2002).

Funatsu, T. et al., "Imaging of single fluorescent molecules and individual APT tunovers by singel myosin molecules in aqueous solution", *Nature*, vol. 374, pp. 555-559 (Apr. 1995).

Garcia, A., "Determination of Ion Penneability by Fluorescence Quenching", *Meth. in Enzymology*, 207:501-511 (1992).

Gardner, A., et al., "Acyclic and dideoxy terminator preferences denote divergent sugar recognition by archaeon and *Taq* DNA polymerases", *Nucleic Acids Research*, vol. 30, No. 2, pp. 605-613 (2002).

Gardner et al., "Comparative kinetics on nucleotide analog incorporation by Vent DNA polymerase," *J. Biol. Chem.*, 279, No. 12, p. 11834-11842 (2004).

Giller et al., "Incorporation of reporter molecule-labeled nucleotides by DNA polymerases. I. Chemical synthesis of various reporter group-labeled 2'deoxyribonucleoside-5'-triphosphates," *Nucleic Acids Res.*, 31, No. 10, p. 2630-2635 (2003).

Giusti, W. et al., "Synthesis and Characterization of 5'-Fluorescent-dye-labeled Oligonucleotides", *PCR Methods and Applications*, 2:223-227 (1993).

Goll et al., "Microvalves with bistable buckled polymer diaphragms," *J. Micromech. Microeng.*, vol.6., pp. 77-79 (1996).

Goodwin, P.M., et al., "Application of single molecule detection to DNA sequencing." *Nucleosides & Nucleotides*, 16(5-6): p. 543-550 (1997).

Gravesen et al., "Microfluidics—a review", *J. Micromech. Microeng.*, vol. 3, pp. 168-182 (1993).

Greene, T.W. and P.G.M. Wuts, "Protective Groups in Organic Synthesis." John Wiley & Sons, Inc.: New York, 1999 3rd Ed.

Gueroui, Z., et al., "Observation by fluorescence microscopy of transcription on single combed DNA," *PNAS*, 99(9): p. 6005-6010 (2002).

Guilbault, G., "Practical Fluorescence—Theory, Methods and Techniques," Chapters 1 and 3, and pp. 521-524, Marcel Dekker, Inc., New York (1973).

Guillier, F., D. Orain, and M. Bradley, "Linkers and Cleavage Strategies in Solid-Phase Organic Synthesis and Combinatorial Chemistry." Chemical Reviews, 100(6): p. 2091-2157 (2000).

Gupta, K.C., et al., "A general method for the synthesis of 3'-sulfhydryl and phosphate group containing oligonucleotides", *Nucleic Acids Res.*, 1901:3019-25 (1991).

Gyllenstein, U. et al., "Generation of single-stranded DNA by the polymerase chain reaction and its application to direct sequencing of the HLA-DQA locus", *PNAS*, 85:7652-56 (1988).

Ha, "Single molecule dynamics studied by polarization modulation," *Phys. Rev. Lett.*, 77, No. 19, 3979-3982 (1996).

Ha, "Single molecule spectroscopy with automated positioning," *Appl. Phys. Lett.* 70, No. 6, 782-784 (1997).

Ha, "Single-molecule fluorescence methods for the study of nucleic acids," Current Opinion in Struct Bio, 11, 287-292 (2001).

Ha et al., "Single-molecule fluorescence spectroscopy of enzyme conformational dynamics and cleavage mechanism," *PNAS*, 96(3): p. 893-898 (1999).

Ha, T., "Single-molecue fluorescence resonance energy transfer," *Methods*, 25(1): p. 78-86 (2001).

Hanna, M. et al., "Synthesis and characterization of a new photocrosslinking CTP analog and its use in photoaffinity labeling *E. coli* and T7 RNA polymerases", *Nucleic Acids Res.*, 21(9):2073-2079 (1993).

Hansen, C.J., et al., "A robust and scalable microfluidic metering method that allows Protein crystal growth by free interface diffusion". Proc Natl Acad Sci U S A, 99 (26): p. 16531-6 (2002).

Harding et al., "Single-molecule detection as an approach to rapid DNA sequencing," Trends in Biotechnology, vol. 10, 3 pages, (1992).

Harris, J.M., "Introduction to Biochemical and Biomedical application of poly(ethylene glycol)." Poly(ethylene glycol) Chemistry, Harris, J. M., Ed.; Plenum Press: New York, pp. 1-14 (1992).

Harrison et al., "Micromachining a miniaturized capillary electrophoresis-based chemical analysis system on a chip," Science, vol. 261, pp. 895-897 (1993).

Harrison, D., et al., "Towards miniaturized electrophoresis and chemical analysis systems on silicon: an alternative to chemical sensors", *Sensors and Actuators B*, 10, pp. 107-116 (1993).

Hasan, A. et al., "Photolabile Protecting Groups for Nucleosides: Synthesis and Photodeprotection Rates", *Tetrahedron*, 53(12):4247-4264 (1997).

Hornbeck, L. et al., "Bistable Defonnable Mirror Device", 1988 Techllical Digest Series, vol. 8, Optical Society of America, pp. 107-110, (Jun. 1988).

Hosokawa et al., "Handling of Picoliter liquid samples in a poly(dimethylsiloxane)-based microfluidic device," Anal. Chem., vol. 71, No. 20, pp. 4781-4785 (1999).

Houseal, T. et al., "Real-time imaging of single DNA molecules with fluorescence microscopy", *Biophys. J.*, vol. 56, pp. 507-516 (Sep. 1989).

Howorka, et al., "Sequence-specific detection of individual DNA strands using engineered nanopores." Nature Biotechnology, 19(7): p. 636-639 (2001).

Hubner et al., "Direct observation of the triplet lifetime quenching of single dye molecules by molecular oxygen," J. Chem. Physics, 115, No. 21, p. 9619-9622 (2001).

Hultman, T. et al., "Bidirectional Solid-Phase Sequencing of In Vitro-Amplified Plasmid DNA", *BioTechniques*, vol. 10, No. 1, pp. 84-93 (1991).

Hyman, E., "A New Method of Sequencing DNA", *Anal. Biochem.*, 174:423-436 (1988).

Ikuta et al., "Three dimensional micro integrated fluid systems (MIFS) fabricated by stereo lithography", *IEEE Kyushu Institute of Technology*, pp. 1-6, (1994).

Ishii et al., "Fluorescence resonance energy transfer between single fluorophores attached to a coiled-coil protein in aqueous solution," Chemical Physics, 247, 163-173 (1999).

Ishijima, A. et al., "Simultaneous Observation of Individual ATPase and Mechanical Events by a Single Myosin Molecule during Interaction with Actin", *Cell*, vol. 92, pp. 161-171, (Jan. 1998).

Ishikawa, M. et al., "Single-Molecule Detection by Laser-Induced Fluorescence Techniques with a Position-Sensitive Photon-Counting Apparatus", *Appl. Phys.*, vol. 33, Part 1, No. 3A, pp. 1571-1576 (1994).

Jacobs et al., "Combinatorial chemistry—applications of light-directed chemical synthesis", *TIBTech*, vol. 1, pp. 19-26 (Jan. 1994).

Jacobson, K. et al., "International Workshop on the application of fluorescence photobleaching techniques to problems in cell biology", Workshop Summary, Federation Proceedings, vol. 42, pp. 72-79 (1983).

Jacobson, et al., "High-speed separations on a microchip," Anal. Chem., vol. 66, No. 7, pp. 1114-1118 (1994).

Jacobson, et al., Microfluidic devices for electrokinetically driven parallel and serial mixing, Anal. Chem., vol. 71, No. 20, pp. 4455-4459 (1999).

Jett, J. et al., "High-Speed DNA Sequencing: An Approach Based Upon Fluorescence Detection of Single Molecules", *J. Biomolecular Structure & Dynamics*, vol. 7, No. 2, pp. 301-309, (1989).

Johnston, R. et al., "Autoradiography using storage phosphor technology", *Electrophoresis*, 11 :355-360 (1990).

Jongeneel, C.V., et al., "Comprehensive sampling of gene expression in human cell lines with massively parallel signature sequencing". Proc Natl Acad Sci U S A, 100(8): p. 636-639 (2003).

Joos, B. et al., "Covalent Attachment of Hybridizable Oligonucleotides to Glass Supports", *Anal. Biochem.* 247(1):96-101 (1997).

Kambara, H. et al., "Optimization of Parameters in a DNA Sequenator using Fluorescence Detection", *Biotechnology*, vol. 6, pp. 816-821 (1988).

Kartalov, Emil P., et al., "Microfluidic device reads up to four consecutive base pairs in DNA sequencing-by-synthesis", *Nucleic Acids Research*, vol. 32, No. 9, pp. 2873-2879 (2004).

Kartalov et al., "Single-Molecule Detection and DNA Sequencing-by-Synthesis," In Partial Fulfillment of the Requirements for the Degree of Doctor Philosophy, California Institute of technology, pp. 1-160 (2004).

Kartalov et al., "Poly-Electrolyte Surface-Chemistry Platform for Fluorescence Studies of DNA on Glass", http://www.ugcs.caltech.edu/~kartalov/PEM_6.pdf, pp. 1-7, last modified Jun. 7, 2002.

Kawai et al., "A simple method of detecting amplified DNA with immobilized probes on microtiter wells", *Analytical Biochemistry*, 209:63-69 (1993).

Kelso et al., "Single-cell analysis by RT-PCR reveals differential expression of multiple type 1 and 2 cytokine genes among cells within polarized CD4d+ T cell populations," International Immunology, 11, No. 4, 617-621 (1999).

Kenis et al., "Microfabrication inside capillaries using multiphase laminar flow patterning," Science, vol. 285, pp. 83-85 (1999).

Kenney, et al., "Mutation Typing Using Electrophoresis and Gel-Immobilized Acrydite™ Probes," BioTechniques, vol. 25, No. 3, pp. 516-521, (1998).

Khandjian, E., "UV cross linking of RNA to nylon membrane enhances hybridization signals", *Mole. Bio, Rep.* 11:107-115 (1986).

Khrapko, K. et al., "A method for DNA sequencing by hybridization with oligonucleotide matrix", *DNA Sequence-J. DNA Sequencing and Mapping*, vol. 1, pp. 375-388 (1991).

Kiefer, J. et al., "Crystal structure of a thermostable *Bacillus* DNA polymerase I large fragment at 2.1 A resolution", *Structure*, 5:95-108 (1997).

Kim, Y. et al., "Crystal structure of *Thermus aquaticus* DNA polymerase", *Nature*, 376:612-616 (1995).

Kirkland, T.A., D.M. Lynn, and R.H. Grubbs, "Ring-Closing Metathesis in Methanol and Water." Journal of Organic Chemistry, 63(26): p. 9904-9909 (1998).

Knerr, L. and R.R. Schmidt, "Application of a ring-closing-metathesis-based linker to the solid phase synthesis of oligosaccharides" Synlett, 11: p. 1802-1804 (1999).

Kopp, et al., "Chemical Amplification: Conitnuous-Flow PCR on a Chip", Science, vol. 280, pp. 1046-1048 (May 1998).

Korolev, S. et al., "Crystal structure of the large fragment of *Thermus aquaticus* DNA polymerase I at 2.5 A resolution: Structural basis for thermo stability", *PNAS*, 92:9264-9268 (1995).

Kovacs et al., "Simple synthesis of 5-vinyl-and 5-ethynyl-2' deoxyuridine 5'-triphosphates", Tetrahedron Letters, 29(36): p. 4525-8 (1988).

Kricka et al., "Labels, Labeling, Analytical Strategies, and Applications." Ch. 1 and Table 1x, Academic Press, New York, pp. 3-40, (1995).

Krider, E. et al., "2'-Modified Nucleosides for Site-Specific Labeling of Oligonucleotides", *Bioconjugate Chem.*, vol. 13, No. 1, pp. 155-162 (2002).

Kuhn, L. et al., "Silicon Charge Electrode Array for Ink Jet Printing", *IEEE Trans. On Electron Dev.*, vol. ED-25, No. 10, pp. 1257-1260 (Oct. 1978).

Lacoste, T. et al., "Ultrahigh-resolution multicolor colocalization of single fluorescent probes", *PNAS*, 97(17):9461-6 (2000).

Lander, E.S., et al., "Initial sequencing and analysis of the human genome." Nature, 409(6822): p. 860-921 (2001).

Lazowski, K. et al., "Highly Sensitive Detection of Hybridization of Oligonucleotides to Specific Sequences of Nucleic Acids by Application of Fluorescence Resonance Energy Transfer", *Antisense and Nucleic Acid Drug Dev.*, vol. 10, pp. 97-103 (2000).

Lee, "Enhancing the catalytic repertoire of nucleic acids: a systematic study of linker length and rigidity," Nucleic Acids Res., 29, No. 7, Apr. 1, 1565-1573 (2001).

Lee, Y. et al., "Laser-Induced Fluorescence Detection of a Single Molecule in a Capillary", *Anal. Chem.*, vol. 66, pp. 4142-4149 (1994).

Levene, M. et al., "Zero-Mode Waveguides for Single-Molecule Analysis at High Concentrations", *Science*, 299:682-686 (Jan. 2003).

Levsky et al., "Single-cell gene expression profiling," Science, 297, 836-840 (2002).

Li, H. et al., "Ultrasensitive Coincidence Fluorescence Detection of Single DNA Molecules", *Anal. Chem.*, 75:1664-1670 (2003).

Li, Y. et al., "Design, Synthesis, and Spectroscopic Properties of Peptide-Bridged Fluorescence Energy-Transfer Cassettes", *Bioconjuate Chem.*, 10:241-245 (1999).

Li, Y. et al., "Structual Studies of the Klentaq1 DNA Polymerase", *Current Organic Chem.*, 5:871-883 (2001).

Li, Z. et al., "A photocleavable fluorescent nucleotide for DNA sequencing and analysis", *PNAS*, vol. 100, No. 2, pp. 414-419 (2003).

Lin, L. et al., "Free-Space Micromachined Optical Switches for Optical Networking", *IEEE J. of Selected Topics in Quanturn Electronics*, vol. 5, No. 1, pp. 4-9 (Jan. 1999).

Liu, J., M.. Enzelberger, and S. Quake, "A nanoliter rotary device for polymerase chain reaction" Electrophoresis, 23(10): p. 1531-6 (2002).

Lodder, M., et al., "Misacylated Transfer RNAs Having a Chemically Removable Protecting Group." Journal of Organic Chemistry, 63(3): p. 794-803 (1998).

Loh, E. et al., "Polymerase Chain Reaction with Single-Sided Specificity: Analysis of T Cell Receptor D Chain", Science 243:217-220 (1989).

Lok, Corie, "Deciphering DNA, Top Speed—Helicos BioSciences aims to expedite sequencing, enable genomic medicine," *Technology Review*, pp. 27-28 (May 2005).

Lopez, G. et al., "Fabrication and Imaging of Two-Dimensional Patterns of Proteins Adsorbed on Self-Assembled Monolayers by Scanning Electron Microscopy", *J. Arner. Chem. Soc.*, 115:10774-81 (1993).

Lotters et al., "The mechanical properties of the rubber eleastic polymer polydimethylsiloxane for sensor applications," J. Micromech. Microeng., vol. 7, pp. 145-147 (1997).

Lucy et al., "Characterization of the cationic surfactant induced reversal of electroosmotic flow in capillary electrophoresis," Anal. Chem., vol. 68, pp. 300-305 (1996).

Ludwig, J and F. Eckstein, "Rapid and Efficient Synthesis of Nucleoside 5'-*O*-(1-Thiotriphosphates), 5'-triphosphates and 2',3'-Cyclophosphorothiaotes Using 2-Chloro-4*H*-1,3,2-benzodioxaphosphorin- 4-one." Journal of Organic Chemistry, 54(3): p. 631-635 (1989).

Lvov, Yu. et al., "Assembly of Thin Films by Means of Successive Deposition of Alternate Layers of DNA and Poly(allylamine)", *American Chemical Society, Macromolecules*, 26, pp. 5396-5399, (1993).

Macklin, J. et al., "Imaging and Times-Resolved Spectroscopy of Single Molecules at an Interface", *Science*, vol. 272, No. 5259, pp. 255-258 (Apr. 1996).

Maier, B., D. Bensimon, and V. Croquette, "Replication by a single DNA polymerase of a streteched single-stranded DNA." Proceedings of the National Academy of Sciences of the United States of America, 97(22): p. 12002-12007 (2000).

Marriott, G. et al., "Time resolved imaging microscopy—Phosphorescence and delayed fluorescence imaging", *Biophys. J.*, vol. 60, pp. 1374-1387 (Dec. 1991).

Marziali, A. and M. Akeson, "New DNA sequencing methods." Annual Review of Biomedical Engineering, 3: p. 195-223 (2001).

Mastrangelo, C. et al., "Vacuum-Sealed Silicon Micromachined Incandescent Light Source", *IDEM*, 89:503-506 (1989).

Meiners, J.C and S.R. Quake, "Femonewton force spectroscopy of single extended DNA molecules." Phys Rev Lett, 84(21): p. 5014-7 (2000).

Meldrum, Kevin, "Microfluidics-based products for nucleic acid analysis", http://www.americanlaboratory.com/articles/al/a9909mel.pdf, 2 pages (Sep. 1999).

Meller, A., et al., "Rapid nanopore discrimination between single polynucleotide molecules." *PNAS*, 93(3): p. 1079-1084 (2000).

Mertz, J. et al., "Single-molecule detection by two-photon-excited fluorescence", *Optics Letters*, vol. 20, No. 24, pp. 2532-2534 (Dec. 1995).

Metzker et al., "Elimination of residual natural nucleotides from 3'-O-modified-dNTP syntheses by enzymatic mop-up," BioTechniques, 25, 814-817 (1998).

Metzker, M.L., et al., "Termination of DNA synthesis by novel 3'-modified-deoxyribonucleoside 5'-triphosphates." Nucleic Acids Res, 22(20): p. 4259-67 (1994).

Mitra, Robi, et al., "Fluorescent in situ sequencing on polymerase colonies", *Analytical Biochemistry*, 320, pp. 55-65 (2003).

Moe et al., Rapid Detection of Clinically Relevant Bacteria in Platelets Using the Hybriscan Baceterial Detection system, Joruanl of the American Society of Hematology, 96, No. 11, 4155 (2000).

Moore, P., "To affinity and beyond", *Nature*, vol. 426, No. 6967, pp. 725-731, (2003).

Muller et al., "Surface-micromachined microoptical elements and systems," IEEE vol. 86, No. 8, pp. 1705-1720 (1998).

Nelson, P. et al., "Bifunctional oligonucleotide probes synthesized using a novel CPG support are able to detect single base pair mutations", *NAR*, 17(18):7187-7194 (1989).

Nie, S. et al., "Probing Individual Molecules with Confocal Fluorescence Microscopy", *Science*, vol. 266, No. 5187, pp. 1018-1021 (Nov. 1994).

Nyren, P. et al., "Solid Phase DNA Minisequencing by an Enzymatic Luminometric Inorganic Pyrophosphate Detection Assay", *Anal. Biochem.*, vol. 208, pp. 171-175 (1993).

Ochman, H. et al., "Genetic Applications of an Inverse Polymerase Chain Reaction", *Genetics* 120:612-623 (1988).

Ohara, To et al, "'Wired' Enzyme Electrodes for Amperometric Determination of Glucose or Lactate in the Presence of interfering Substances",*Anal. Chem.*, vol. 66, No. 15, pp. 2451-2457 (Aug. 1994).

Ohara, T. et al., "Glucose Electrodes Based on Cross-Linked [Os(bpY)2CltH Complexed Poly(1-vinylimidazole) Films", *Anal. Chem.*, vol. 65, pp. 3512-3517 (1993).

Okabe, S. et al., "Do Photobleached Fluorescent Microtubules Move?: Rev-evaluation of Fluorescence Laser Photobleaching both In Vitro and in Growing Xenopus Axon", *J. Cell Bio.*, vol. 120, No. 5, pp. 1177-1186 (1993).

Ollis, D. et al., Structure of large fragment of *E. coli* DNA polymerase I complexed with Dtmp, *Nature*, 313:762-766 (1985).

Oroskar, A. et al., "Detection of immobilized amplicons by ELISA-like techniques" *Clin. Chem.*, 42(9):1547-1555 (1996).

Patchornik, A. et al., "Photosensitive Protecting Groups" *J. Amer. Chem. Soc.*, 92(21):6333-37 (1970).

Padmaja, T., et al., "Enzymatically degradable prodrugs: a novel methodology for drug linkage." Journal of Applies Polymer Science, 85(10): p. 2108-2118 (2002).

Pennisi, E., "Gene rescarchers hunt bargins, fixer-uppers." Science, 298(5594): p. 735-736 (2002).

Perales et al., "Enhancement of DNA, cDNA synthesis and fidelity at high temperatures by a dimeric single-stranded DNA-binding protein," Nucleic Acids Res., 31, No. 22, 6473-6480 (2003).

Perkins, T. et al., "Relaxation of a Single DNA Molecule Observed by Optical Microscopy", *Science*, 264:822-826 (May 1994).

Pethig, R. et al, "Applications of dielectrophoresis in biotechnology", *Tibtech*, vol. 15, pp. 426-432 (Oct. 1997).

Pisani, F. et al, "Domain Organization and DNA-Induced Conformational Changes of an Archaeal Family B DNA Polymerase", *Biochemistry*, vol. 35, pp. 9158-9166 (Jul. 1996).

Plakhotnik, T. et al, "Single-Molecule Spectroscopy", *Annu. Rev. Phys. Chem.*, vol. 48, pp. 181-212 (1997).

Ploem, J., Ch. 1 "Fluorescence Microscopy", Fluorescent and Luminescent Probes for Biological Activity, Mason, T. Ed., Academic Press, London, pp. 1-11 (1993).

Qin et al., "Elastomeric Light Valves," *Advanced Materials*, vol. 9, No. 5, pp. 407-410 (1997).

Qin, P. et al., "Site-Specific Labeling of RNA with Fluorophores and Other Structural Probes", *Methods*, vol. 18, No. 1, pp. 60-70 (May 1999).

Quake, S. et al., "Fluorescent Photobleaching Method for Sequencing DNA", pp. 1-10, circa 1996.

Quake, Stephen R. et al., "Methods and Apparatuses For Analyzing Polynucleotide Sequences", pending U.S. Appl. No. 09/707,737, filed Nov. 6, 2000.

Quake, S. et al., "Polymer Physics with Single Molecules of DNA" (Dept. of Physics), a colloquium by Stephen Quake, Stanford University, Feb. 22, 1996. (Presented at Laser Spectroscopy XII Intl. Conference, Italy, Jun. 1995.).

Quake, S. et al., "From Micro- to Nanofabrication with Soft Materials", *Science*, vol. 290, No. 5496, pp. 1536-1540 (Nov. 2000).

Rapp, R. et al., "LIGA micropump for gases and liquids", *Sensors and Actuators A*, vol. 40, pp. 57-61 (1994).

Rasolonjatovo I. and S.R. Sarfati, "6-N-(N-methylanthranyamido)-4-oxo-hexanoic acid: a new florestein protecting group applicable to a new DNA sequencing method." Nucleosides & Nucleotides, 17(9-11): p. 2021-2025 (1998).

Rasolonjatovo, I. and Sarfati, "Development of a new DNA sequencing method: 3'-ester cleavage catalyzed by Taq DNA polymerase." Nucleosides & Nucleotides 18(4 & 5): p. 1021-1022 (1999).

Reha-Krantz, L. et al., "Genetic and Biochemical Studies of Bacteriophage T4 DNA Polymerase 3'→5'-Exonuclease Activity", *The Journal of Biological Chemistry*, vol. 268, No. 36, pp. 27100-27108 (1993).

Reha-Krantz, L. et al., "Motif A of Bacteriophage T4 DNA Polymerase: Role in Primer Extension and DNA Replication Fidelity", *The Journal of Biological Chemistry*, vol. 269, No. 8, pp. 5635-5643 (1994).

Rigler, R, et al, "DNA-sequencing at the single molecule level." Journal of Biotechnology, 86(3): p. 161 (2001).

Rigler, R., "Fluorescence correlations, single molecule detection and large number screening—Applications in Biotechnology", *J. Biotech.*, 41: 177-186 (1995).

Ronaghi, M. et al., "A Sequencing Method Based on Real-Time Pyrophosphate", *Science*, vol. 281, pp. 363-365 (Jul. 1998).

Ronaghi, M et al., "Real-Time DNA Sequencing Using Detection of Pyrophosphate Release," *Analytical BioChemistry.* 242, No. 0432, (1996).

Rosenblum, B. et al., "New dye-labeled terminators for improved DNA sequencing patterns", *Nucleic Acids Research*, vol. 25, No. 22, pp. 4500-4504 (Nov. 1997).

Rosenblum, B. et al., "Improved single-strand DNA sizing accuracy in capillary electrophoresis", *Nucleic Acids Research*, vol. 25, No. 19, pp. 3925-3929 (Oct. 1997).

Roylance, L. et al., "A Batch-Fabricated Silicon Accelerometer", *IEEE Trans. On Elec. Dev.*, vol. ED-26, No. 12, pp. 1911-1917 (1979).

Ruparel, Hameer, "Design and synthesis of a 3'-$O$-allyl photocleavable fluorescent nucleotide as a reversible terminator for DNA sequencing by synthesis", *PNAS*, vol. 102, No. 17, pp. 5932-5937 (Apr. 26, 2005).

Ruth, J. et al., "Nucleoside Analogues with Clinical Potential in Antivirus Chemotherapy", *Molecular Pharmacology*, 20:415-422 (1981).

Sanger, F. et al., "DNA sequencing with chain-terminating inhibitors", *PNAS*, 74(12):5463-67 (Dec. 1977).

Sarfati, S.R., et al., "Synthesis of fluorescent derivatives of 3'-$O$-(6-aminohexanoyl)-pyrimidine nucleosides 5'-triphosphates that act as DNA polymerase substrates reversibly tagged at C-3'." Journal of the Chemical Society, Perkin Transactions 1: Organic and Bio-Organic Chemistry, 9: p. 1163-71 (1995).

Sato, E. et al., "Bimane Conjugates of 5-Halogenouridylic Acids as Fluorogenic Substrates for Phosphodiesterase I", *J. Chem. Research (S)*, Issue 10, pp. 390-391 (1994).

Satoh, Ikuo et al., "Flow-injection determination of inorganic pyrophosphate with use of an enzyme thermistor containing immobilized inorganic pyrophosphatase", *Chemical Abstracts*, vol. 110, No. 16, pp. 409-413 (1988).

Sauer, M., et al., "Single molecule DNA sequencing in submicrometer channels: state of the art and future prospects." Journal of Biotechnology, 86(3): p. 181-201 (2001).

Schasfoort et al., "Field-effect flow control for microfabricated fluidic networks," Science, vol. 286, pp. 942-945 (1999).

Schueller, O., et al., "Reconfigurable diffraction gratings based on elastomeric microfluidic devices", *Sensors and Actuators*, 78, pp. 149-159 (1998).

Seeger, S. et al., "Single molecule fluorescence—High Performance Molecular Diagnosis and Screening", translated from *BIOforum*, pp. 179-185, (Apr. 1998).

Selvin, P., "Fluorescence Resonance Energy Transfer", *Meth. In Enzymology*, vol. 246, pp. 300-335, Academic Press (1995).

Seo, Tae Seok, "Four-color DNA sequencing by synthesis on a chip using photocleavable fluorescent nucleotides", *PNAS*, vol. 102, No. 17, pp. 5926-5931 (Apr. 26, 2005).

Seo, Tae Seok, "Photocleavable fluorescent nucleotides for DNA sequencing on a chip constructed by site-specific coupling chemistry", *PNAS*, vol. 101, No. 15, pp. 5488-5493 (Apr. 13, 2004).

Shackelford, James F., "Intro. to Materials Science for Engineers," 3$^{rd}$ Edition, Prentice-Hall, Inc., Mamillan Publ. Co. (1992) (cited by Examiner E. Quan in related case).

Shendure et al., "Advanced sequencing technologies: Methods and goals," *Nature Reviews*, vol. 5, No. 5, pp. 335-344 (2004).

Shoji, S. et al., "Smallest Dead Volume Microvalves for Integrated Chemical Analyzing Systems", *Proceedings of Tranducers '91*, IEEE, pp. 1052-1055, San Francisco (1991).

Shoji, S. et al., "Fluids for Sensor Systems." Microsystem Technology in Chemistry and Life Science, Topics in Current Chem., vol. 194, pp. 162-188, Springer-Verlag (1998).

Smith, L. et al., "Fluorescence detection in automated DNA sequence analysis", Nature, vol. 321, pp. 674-679 (Jun. 1986).

Smith, L. et al., "The synthesis of oligonucleotides containing an aliphatic amino group at the 5' terminus: synthesis of fluorescent DNA primers for use in DNA sequence analysis", Nucleic Acids Res., vol. 13, No. 7, pp. 2399-2412 (1985).

Smith, S. et al., "Direct Mechanical Measurements of the Elasticity of Single DNA Molecules by Using Magnetic Beads", Science 258:1122-26 (1992).

Smits, I., "Piezoelectric Micropump with Three Valves Working Peristaltically", Sensors and Actuators, vol. A21-A23, pp. 203-206 (1990).

Song et al., "Influence of the triplet excited state on the photobleaching kinetics of fluorescein in microscopy," Biophysics J., 70, 2959-2968 (1996).

Sproat, B. et al., "The synthesis of protected 5'-mercapto-2',5'-dideoxyribonucleoside- 3'-O-phosphoramidities; use of 5'-mercapto-oligodeosyribonucleotides", Nucleic Acids Res., 15(12):4837-48 (1987).

Stocki, S. et al., "Dynamics of Bacteriophage T4 DNA Polymerase Function: Identification of Amino Acid Residues that Affect Switching between Polymerase and 3'→='- Exonuclease Activities", J. Mol. Biol., 254, pp. 15-28 (1995).

Strausberg, R L, et al., "The mammalian gene collection." Science, 286(5439): p. 455-7 (1999).

Sukhorukov, G.B., et al., "Assembly of polyelectrolyte multilayer films by consecutively alternating adsorption of polynucleotides and polycations", Thin Solid Films, 284-285, pp. 220-223 (1996).

Tasara et al., "Incorporation of reporter molecule-labeled nucleotides by DNA polymerases. II. High-density labeling of natural DNA," Nucleic Acids Res., 31, No. 10, 2636-2646 (2003).

Taveira, N. et al., "Detection of HI VI proviral DNA by PCR and hybridization with digoxigenin labeled probes", Mol. Cell Probes, vol. 6, No. 4, pp. 265-270 (1992).

Taylor, D. et al., "Characterization of chemisorbed monolayers by surface potential measurements", J. Phys. D. Appl. Phys. 24:1443-50 (1991).

Terry, S. et al., "A Gas Chromatographic Air Analyzer Fabricated on a Silicon Wafer", IEEE Trans. on Electron Dev., vol. ED-26, No. 12, pp. 1880-1886 (1979).

Theisen, P. et al., "Fluorescent dye phosphoramidite labeling of oligonucleotides", Nucleic Acids Symp. Ser., vol. 27, pp. 99-100 (1992).

Thompson, N. et al., "Measuring Surface Dynamics of Biomolecules by Total Internal Reflection Fluorescence with Photobleaching Recovery or Correlation Spectroscopy", Biophys. J., vol. 33, pp. 435-454 (Mar. 1981).

Thompson, N. et al., "Immunoglobulin Surface-Binding Kinetics Studied by Total Internal Reflection with Fluorescence Correlation Spectroscopy", Biophys. J., vol. 43, pp. 103-114 (Jul. 1983).

Thoresen, T. S.J. Maerkl, and S.R. Quake, "Microfluidic large-scale integration." Science, 298(5593): p. 580-4 (2002).

Tokunaga, M. et al., "Single Molecule Imaging of Fluorophores and Enzymatic Reactions Achieved by Objective-Type Total Internal Reflection Fluorescence Microscopy", Biochem. And Biophys. Res. Comm., vol. 235, pp. 47-53 (1997).

Tolneguzzo, F. et al., "Use of a Chemically Modified T7 DNA Polymerase for Manual and Automated Sequencing of Super coiled DNA", BioTech, vol. 6, No. 5, pp. 460-469 (1988).

Trager, R. S., "DNA sequencing—Venter'next goal: 1000 human genomes." Science, 298(5595): p. 947 (2002).

Tufte, O. et al., "Silicon Diffused-Element Piezoresistive Diaphragms", J. Applied Phys., vol. 31, No. 11, pp. 3322-3327 (Nov. 1962).

Tyagi, S. et al. "Multicolor molecular beacons for allele discrimination", Nat. Biotechnol., 16:49-53 (1998).

Ullman's Encyclopedia of industrial Chemistry, 6ID Edition, vol. 6, Sections 6 to 6.3, Subject: Carbon Black, Wiley, VCH (1999).

Unger et al., "Monolithic microfabricated valves and pumps by multilayer soft lithography,"Science 288: 113-116 (2000).

Unger, M. et al., "Single-Molecule Fluorescence Observed with Mercury Lamp Illumination", BioTechniques, vol. 27, PD. 1008-1014 (Nov. 1999).

Vale, R. et al., "Direct observation of single kinesin molecules moving along microtubles", Nature, vol. 380, pp. 451-453, (Apr. 1996).

Van Dam, R.M. and S.R Quake, "Gene expression analysis with universal n-mer arrays." Genome Res, 12(1): p. 145-152 (2002).

Van de Pol, F. et al., "Micro-liquid handling devices: A Review", Micro System Technologies 90, 1st Intl. Conf. On Micro Electro, Opto, Mechanic Systems and Components, pp. 799-805, Berlin, Springer-Verlag, (1990).

Van Oijen et al., "Single molecule kinetics of λ exonuclease reveal base dependence and dynamic disorder," Science, 301, 1235-1238 (2003).

Venter, J.L., et al., "The sequence of the human genome." Science, 291(5507): p. 1304-1351 (2001).

Vieider, C. et al., "A Pneumatically Actuated Micro Valve With A Silicone rubber Membrane For Integration With Fluid-Handling Systems", Proceedings of Transducers '95, pp. 284-286, Stockholm (1995).

Walker, M.G., et al., "Prediction of gene function by genome-scale expression analysis: Prostate cancer-associated genes.": Genome Researce, 9(12): p. 1198-1203 (1999).

Wang, G. et al., "Design and Synthesis of New Fluorogenic HIV Protease Substrates Based on Resonance Energy Transfer", Tetrahedron Lett., 31(45):6493-96 (1990).

Wang, M.D., et al., "Force and Velocity measured for single molecules of RNA polymerase." Science, 282(5390): p. 902-907 (1998).

Washizu et al., "Molecular dielectrophoresis of biopolymers," IEEE Transactions on Industry Applications, vol. 30, No. 4, pp. 835-843 (1994).

Watkins, R. et al., "A Total Internal-Reflection Technique for the Examination of Protein Adsorption", J. Biomed. Mater. Res., vol. 11, pp. 915-938 (1977).

Weber, J.L. and E.W. Myers, "Human whole-genome shotgun sequencing." Genome Research, 7(5): p. 401-409 (1997).

Webster, J. et al., "Monolithic Capillary Gel Electrophoresis Stage with On-Chip Detector", Intl. Conf. on MEMS (MEMS 96), pp. 491-496 (1996).

Wedekind, P. et al., "Scanning microphotolysis: a new photobleaching technique based on fast intensity modulation of a scanned laser beam and confocal imaging", J. Microscopy, vol. 176, Pt. 1, pp. 23-33 (Oct. 19940.

Weir, et al., "Hybrigel Purification: A Novel Technique of Accelerated Prepartion for DNA Sequence Products for Capillary Electrophoresis and Multiplexing," Clinical Chemistry, vol. 45, No. 11, p. 2052 (1999).

Weiss, S., "Fluorescence Spectroscopy of Single Biomolecules", Science, vol. 283, pp. 1676-1683 (Mar. 1999).

Welch, M.B. and K. Burgess, "Synthesis of fluorescent, photolabile 3'-O-protected nucleoside triphosphates for the base addition sequencing scheme." Nucleosides & Nucleotides, 18(2): p. 197-201 (1999).

Werner et al "Progress towards single-molecule DNA sequencing: a one color demonstration." J Biotechnol, 102(1): p. 1-14 (2003).

Williams, N. et al., "Exploring the Adenine Nucleotide Binding Sites on Mitochondrial $F_1$-ATPase with a New Photoaffinity Probe, 3'-O-(4-Benzoyl)benzoyl Adenosine 5'-Triphosphate", J. Bioi. Chem., 237(6):2834-41 (1982).

Winter et al., "Direct gene expression analysis," Curr. Pharm. Biotech., 5, p. 191-197 (2004).

Wu, et al., "Synthesis and Properties of Adenosine-5'-triphosphoro-γ-l-(5-sulfonic acid)naphthyl Ethylamide: A Fluorescent Nucleotide Substrate for DNA-Dependent RNA Polymerase from Escherichia coli," Archives of Biochemistry and Biophysics, vol. 246, No. 2, pp. 564-571 (1986).

Wuite, G. et al., "Single-molecule studies of the effect of template tension on T7 DNA polymerase activity", Nature 404:103-6 (2000).

Xia et al., "Complex optical surfaces formed by replica molding against elastomeric masters," Science vol. 273, pp. 347-349 (1996).

Xia et al. "Soft Lithography," Angew. Chem. Int. Ed. vol. 37, pp. 550-575 (1998).

Xia, G., et al., "Directed evolution of novel polymerase activities: mutation of a DNA polymerase into a efficient RNA polymerase." Proc Natl Acad Sci USA; 99(10) p. 6597-6602 (2002).

Xie, "Single molecule approach to dispersed kinetics and dynamic disorder: Probing conformational fluctuation and enzymatic dynamics," J. Chem. Physics, 117, No. 24, p. 11024-11032 (2002).

Xu, X. et al., "Direct Measurement of Single-Molecule Diffusion and Photodecomposition in Free Solution", *Science*, vol. 275, pp. 1106-1109, (Feb. 1997).

Xu, X. et al., "Long-Range Electrostatic Trapping of Single-Protein Molecules at a Liquid-Solid Interface", *Science*, vol. 281, pp. 1650-1653 (Sep. 1998).

Yang et al., "A Mems Thermopneumatic Silicone Rubber Membrane Valve", Proceedings of IEEE 10th Annual International Workshop on MicroElectro Mechanical Systems, Sensors and Actuators, vol. A64, No. 1, pp. 101-108 (1998).

Yazdi, N. et al., "Micromachined Intertial Sensors", *Proceedings of the IEEE*, vol. 86, No., pp. 1640-1659 (Aug. 1998).

Yershov, G. et al., "SNA analysis and diagnostics on oligonucleotide microchips", *Proc. Natl. Acad. Sci. USA*, vol. 93, pp. 4913-4918 (May 1996).

Young et al., "Contoured elastic-membrane microvalves for microfluidic network integration," J. Biomechanical Engineering, vol. 121, pp. 2-6 (1999).

Yu., et al., "Cyanine dye dUTP analogs for enzymatic labeling of DNA probes." Nucleic Acids Res, 22(15): p. 3226-32 (1994).

Zdeblick, M. et al., "A Microminiature Electric-To-Fluidic Valve", Transducers '87, reprinted in *Micromechanics and MEMS Classic and Seminal Papers to 1990*, IEEE Press, pp. 437-439 (1987).

Zhu, Z. et al., "Molecular Mechanism Controlling the Incorporation of Fluorescent Nucleotides into DNA by PCR", *Cytometry*, 28:206-211 (1997).

Zhu, Z. et al., "Directly labeled DNA probes using fluorescent nucleotides with different length linkers", *Nucleic Acids Res.*, vol. 22, No. 16, pp. 3418-3422 (1994).

Zuckerman, R. et al., "Efficient methods for attachment of thiol specific probes to the 3' ends of synthetic oligodeoxyribonucleotides", *Nucleic Acids Res.*, 15(13):5305-5321 (1987).

Therminator DNA Polymerase FAQ, http://www.neb.com/nebecomm/products/faqproductM0261.asp downloaded Jun. 1, 2005, 1 page.

* cited by examiner

NUCLEOTIDE ANALOGS

FIELD OF THE INVENTION

The invention relates to nucleotide analogs and methods for sequencing a nucleic acid using nucleotide analogs.

BACKGROUND

There have been proposals to develop new sequencing technologies based on single-molecule measurements. For example, sequencing strategies have been proposed that are based upon observing the interaction of particular proteins with DNA or by using ultra high resolution scanned probe microscopy. See, e.g., Rigler, et al., J. Biotechnol., 86(3):161 (2001); Goodwin, P. M., et al., Nucleosides & Nucleotides, 16(5-6):543-550 (1997); Howorka, S., et al., Nature Biotechnol., 19(7):636-639 (2001); Meller, A., et al., Proc. Nat'l. Acad. Sci., 97(3):1079-1084 (2000); Driscoll, R. J., et al., Nature, 346(6281):294-296 (1990).

Recently, a sequencing-by-synthesis methodology has been proposed that resulted in sequence determination, but not with consecutive base incorporation. See, Braslavsky, et al., Proc. Nat'l Acad. Sci., 100: 3960-3964 (2003). An impediment to base-over-base sequencing has been the use of bulky fluorophores that can sterically hinder sequential base incorporation. Even when the label is cleaved, some fluorescently-labeled nucleotides sterically hinder subsequent base incorporation due to the residue of the linker left behind after cleavage.

A need therefore exists for nucleotide analogs having reduced steric hindrance, thereby allowing the polymerase to produce greater read-length from each template.

SUMMARY OF THE INVENTION

The present invention provides nucleotide analogs and methods of using nucleotide analogs in sequencing. A nucleotide analog of the invention features a cleavable linker between the base portion of the nucleotide and the label.

In general, nucleotide analogs comprise an inhibitory molecule that reduces the likelihood of subsequent incorporation of a second nucleotide or nucleotide analog to a primer during sequencing-by-synthesis. Preferably, the inhibitory molecule is removable so that additional incorporation of nucleotides or nucleotide analogs may be accomplished. According to the invention, the inhibitory molecule can be attached anywhere on the nucleotide analogs so long as it inhibits the subsequent addition of additional nucleotides or nucleotide analogs. A preferred inhibitory molecule is a dideoxynucleotide, however any appropriate inhibitory can be used according to the invention, such as, for example, a label. In general, an inhibitory molecule includes any molecule that provides sterically hinders the subsequent incorporation of additional nucleotides or nucleotide analogs during sequencing-by-synthesis. Functionally, in some embodiments, an inhibitory molecule can block the active site of the polymerase thereby inhibiting or limiting the incorporation of additional nucleotides or nucleotide analogs. Subsequent addition of nucleotides and nucleotide analogs can be accomplished after removing the inhibitory molecule.

In a preferred embodiment, a nucleotide analog of the invention is a nucleotide triphosphate comprising an optically-detectable label attached to the nitrogenous base portion of the nucleotide via a cleavable linker. Examples of preferred linkers are provided below.

Cleavage may be accomplished via any appropriate method and/or combination of methods. Specific examples are provided below. For example, a cleavage site may be chemically cleavable, photolytically cleavable, or mechanically cleavable (i.e., by shaking). Chemical cleaving can be accomplished by exposing the linker to one or more pH level. The cleavable bond can be cleaved upon exposure to a pH of from about 11.3 to about 12.3, more particularly upon exposure to a pH of about 11.8. A preferred cleavage site is a carboxyl nitrogen bond, which can be positioned in the linker in order to effect the purposes of the invention.

Any detectable label can be used in practice of the invention. Optically-detectable labels, and particularly fluorescent labels, are highly preferred. The base is selected from the group consisting of a purine, a pyrimidine and derivatives. Analogs of the invention may be further modified by inclusion of a blocking group at the 3' hydroxyl position on the sugar moiety of the nucleotide. For example, a preferred analog comprises a phosphate group in place of the hydroxyl group in the 3' position of the nucleotide sugar.

In general, methods of using nucleotide analogs of the invention comprise exposing a target nucleic acid/primer duplex to one or more nucleotide analogs and a polymerase under conditions suitable to extend the primer in a template dependent manner. Any appropriate polymerase can be used according to the invention. For example, in one embodiment, a Klenow fragment with reduced exonuclease activity is used to extend the primer in a template-dependent manner. Generally, the primer is, or is made to be, sufficiently complementary to at least a portion of the target nucleic acid to hybridize to the target nucleic acid and allow template-dependent nucleotide polymerization. The primer is extended by one or more bases.

In one embodiment, a labeled nucleotide analog having a linker with a cleavable bond with a carboxyl nitrogen bond is incorporated into a primer portion of a nucleic acid duplex comprising a template to be hybridized to the primer. The incorporated labeled nucleotide is identified and the cleavable bond is cleaved. The incorporating, identifying, and cleaving steps are repeated at least one time and a sequence of the target nucleic acid/primer duplex is determined based upon the order of the incorporation of the labeled nucleotides. The cleaving step can include exposing the cleavable bond to a pH of from about 11.3 to about 12.3, preferably, exposing the cleavable bond to a pH of about 11.8. Optionally, the cleaved bond is capped (for example, with an alkylating agent), rendering it unreactive. Common alkylating agents, such as iodoacetamide, are used to cap the cleaved bond.

In single molecule sequencing, the template nucleic acid molecule/primer duplex is immobilized on a surface such that nucleotides (or nucleotide analogs) added to the immobilized primer are individually optically resolvable. Either the primer, template and/or nucleotide analogs can be detectably labeled such that the position of the duplex is individually optically resolvable. The primer can be attached to the solid support, thereby immobilizing the hybridized template nucleic acid molecule, or the template can be attached to the solid support thereby immobilizing the hybridized primer. The primer and template can be hybridized to each other prior to or after attachment of either the template or the primer to the solid support. The detectable label preferably is optically-detectable, and most preferably is a fluorescent label. Examples of appropriate fluorescent labels include cyanine, rhodamine, fluorescien, coumarin, BODIPY, alexa, conjugated multi-dyes, or any combination of these.

Where an optional phosphate group is present in place of the hydroxyl in the 3' position of the nucleotide sugar, the optional phosphate moiety is removed, preferably enzymatically, after incorporation in order to allow subsequent incorporations. The incorporated nucleotide analog can be detected before, during, or after removing the optional phosphate group.

The primer extension process can be repeated to identify additional nucleotide analogs in the template. The sequence of the template is determined by compiling the detected nucleotides, thereby determining the complimentary sequence of the target nucleic acid molecule.

In general, methods for facilitating the incorporation of a nucleotide analog in a primer include exposing a target nucleic acid/primer duplex to one or more nucleotide analogs of the present invention and a polymerase under conditions suitable to extend the primer in a template dependent manner. Generally, the primer is sufficiently complementary to at least a portion of the target nucleic acid to hybridize to the target nucleic acid and allow template-dependent nucleotide polymerization.

While the invention is exemplified herein with fluorescent labels, the invention is not so limited and can be practiced using nucleotides labeled with any detectable label, including chemiluminescent labels, luminescent labels, phosphorescent labels, fluorescence polarization labels, and charge labels.

A detailed description of the certain embodiments of the invention is provided below. Other embodiments of the invention are apparent upon review of the detailed description that follows.

DETAILED DESCRIPTION OF THE INVENTION

The invention relates to nucleotide analogs that, when used in sequencing reactions, allow extended base-over-base incorporation into a primer in a template-dependent sequencing reaction. Analogs of the invention are useful in sequencing-by-synthesis reactions in which consecutive based are added to a primer in a template-dependent manner.

Nucleotide Analogs

Figure 1:
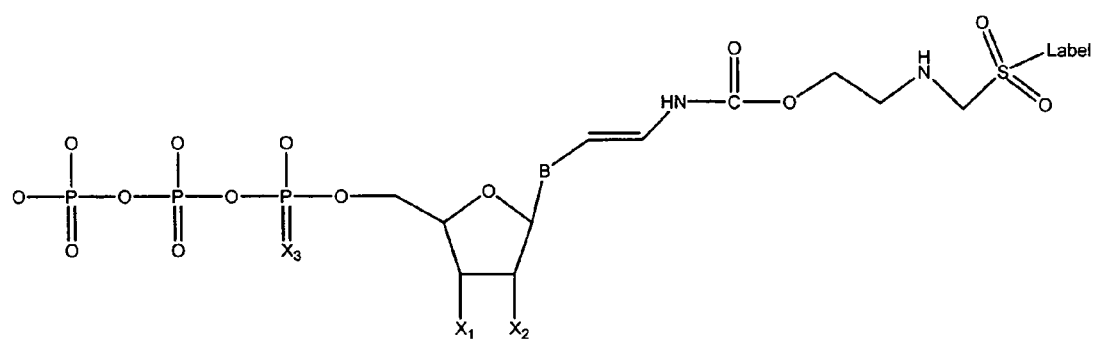
FIG. 1 shows exemplary chemical structures of nucleotide analogs of the present invention having a linker between the base B and the label.

Preferred nucleotide analogs of the invention have the generalized structure (also as shown in FIG. 1):

The base B can be, for example, adenine, cytosine, guanine, thymine, uracil, or hypoxanthine. The base B can also be, for example, naturally-occurring and synthetic derivatives of the preceding group, including pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; and 1,3,5 triazine. Bases useful according to the invention permit a nucleotide that includes that base to be incorporated into a polynucleotide chain by a polymerase and will form base pairs with a base on an antiparallel nucleic acid strand. The term base pair encompasses not only the standard AT, AU or GC base pairs, but also base pairs formed between nucleotides and/or nucleotide analogs comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the nucleotide analog inosine and adenine, cytosine or uracil, where the two hydrogen bonds are formed.

Other preferred nucleotide analogs of the invention have the generalized structure:

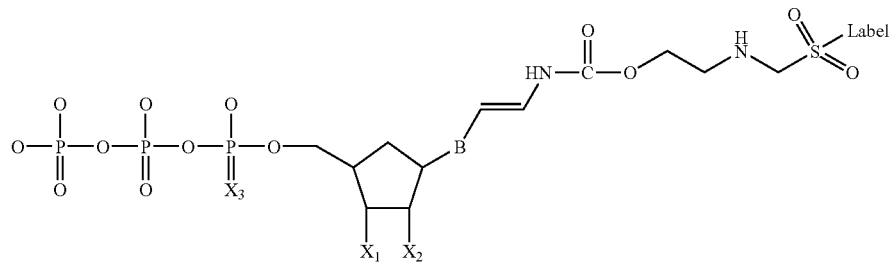

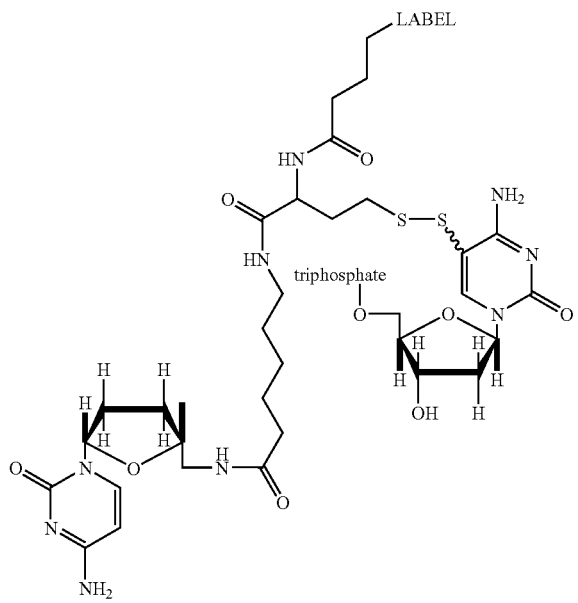

Label for use with the invention preferably is a detectable label. In one embodiment, the label is an optically-detectable label such as a fluorescent label. The label can be selected from detectable labels including cyanine, rhodamine, fluorescien, coumarin, BODIPY, alexa, conjugated multi-dyes, or any combination of these. However, any appropriate detectable label can be used according to the invention, and are known to those skilled in the art.

Nucleic Acid Sequencing

The invention also includes methods for nucleic acid sequence determination using the nucleotide analogs described herein. The nucleotide analogs of the present invention are particularly suitable for use in single molecule sequencing techniques. In general, methods for nucleic acid sequence determination comprise exposing a target nucleic acid (also referred to herein as template nucleic acid or template) to a primer that is complimentary to at least a portion of the target nucleic acid, under conditions suitable for hybridizing the primer to the target nucleic acid, forming a template/primer duplex.

Target nucleic acids include deoxyribonucleic acid (DNA) and/or ribonucleic acid (RNA). Target nucleic acid molecules can be obtained from any cellular material, obtained from an animal, plant, bacterium, virus, fungus, or any other cellular organism. Target nucleic acids may be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid molecules may also be isolated from cultured cells, such as a primary cell culture or a cell line. The cells from which target nucleic acids are obtained can be infected with a virus or other intracellular pathogen.

A sample can also be total RNA extracted from a biological specimen, a cDNA library, or genomic DNA. Nucleic acid typically is fragmented to produce suitable fragments for analysis. In one embodiment, nucleic acid from a biological sample is fragmented by sonication. Test samples can be obtained as described in U.S. Patent Application 2002/0190663 A1, published Oct. 9, 2003, the teachings of which are incorporated herein in their entirety. Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). Generally, target nucleic acid molecules can be from about 5 bases to about 20 kb. Nucleic acid molecules may be single-stranded, double-stranded, or double-stranded with single-stranded regions (for example, stem- and loop-structures).

Any polymerase and/or polymerizing enzyme may be employed. A preferred polymerase is Klenow with reduced exonuclease activity. Nucleic acid polymerases generally useful in the invention include DNA polymerases, RNA polymerases, reverse transcriptases, and mutant or altered forms of any of the foregoing. DNA polymerases and their properties are described in detail in, among other places, DNA Replication 2nd edition, Kornberg and Baker, W. H. Freeman, New York, N.Y. (1991). Known conventional DNA polymerases useful in the invention include, but are not limited to, *Pyrococcus furiosus* (Pfu) DNA polymerase (Lundberg et al., 1991, Gene, 108: 1, Stratagene), *Pyrococcus woesei* (Pwo) DNA polymerase (Hinnisdaels et al., 1996, Biotechniques, 20:186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent™ DNA polymerase, Cariello et al., 1991, Polynucleotides Res, 19: 4193, New England Biolabs), 9° Nm™ DNA polymerase (New England Biolabs), Stoffel fragment, ThermoSequenase® (Amersham Pharmacia Biotech UK), Therminator™ (New England Biolabs), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteoriol, 127: 1550), DNA polymerase, *Pyrococcus kodakaraensis* KOD DNA polymerase (Takagi et al., 1997, Appl. Environ. Microbiol. 63:4504), JDF-3 DNA polymerase (from *thermococcus* sp. JDF-3, Patent application WO 0132887), *Pyrococcus* GB-D (PGB-D) DNA polymerase (also referred as Deep Vent™ DNA polymerase, Juncosa-Ginesta et al., 1994, Biotechniques, 16:820, New England Biolabs), UlTma DNA polymerase (from *thermophile Thermotoga maritima*; Diaz and Sabino, 1998 Braz J. Med. Res, 31:1239; PE Applied Biosystems), Tgo DNA polymerase (from *thermococcus gorgonarius*, Roche Molecular Biochemicals), *E. coli* DNA polymerase I (Lecomte and Doubleday, 1983, Polynucleotides Res. 11:7505), T7 DNA polymerase (Nordstrom et al., 1981, J. Biol. Chem. 256:3112), and archaeal DP1I/DP2 DNA polymerase II (Cann et al., 1998, Proc Natl Acad. Sci. USA 95:14250→5).

Other DNA polymerases include, but are not limited to, ThermoSequenase®, 9° Nm™, Therminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof. Reverse transcriptases useful in the invention include, but are not limited to, reverse transcriptases from HIV, HTLV-1, HTLV-II, FeLV, FIV, SIV, AMV, MMTV, MoMuLV and other retroviruses (see Levin, Cell 88:5-8 (1997); Verma, Biochim Biophys Acta. 473:1-38 (1977); Wu et al., CRC Crit. Rev Biochem. 3:289-347 (1975)).

Unincorporated nucleotide analog molecules are removed prior to or after detecting. Unincorporated nucleotide analog molecules can be removed by washing.

The template/primer duplex is then treated such that the label is removed or the linker is cleaved, partially removed and/or degraded. The steps of exposing template/primer duplex to one or more nucleotide analogs and polymerase, detecting incorporated nucleotides, and then treating to (1) remove and/or degrade the label, (2) remove and/or degrade the label and at least a portion of the linker or (3) cleave the linker can be repeated, thereby identifying additional bases in the template nucleic acid, the identified bases can be compiled, thereby determining the sequence of the target nucleic acid. In some embodiments, the remaining linker and label are not removed, for example, in the last round of primer extension.

The above-described methods for sequencing a nucleic acid template can further include a step of capping the cleavable bond for example, after the bond has been cleaved. The methods for sequencing a nucleic acid template may employ a detectable label selected from, for example, cyanine, rhodamine, fluorescien, coumarin, BODIPY, alexa, conjugated multi-dyes or any combination of these. The template can be individually optically resolvable and is optionally attached to a surface.

In one embodiment, the cleavable linker has a carboxyl nitrogen bond that is chemically cleavable and the linker is cleaved by exposing the extended primer to a pH of about 11.8, thereby causing the removal of the label and at least a portion of the linker from the incorporated nucleotide analog.

Scheme 1

In one embodiment, according to Scheme 1, the linker features a cleavable bond, for example, a carboxyl nitrogen bond, which is located between about 10 atoms and about 1 atom from the uridine base. The carboxyl nitrogen bond can be cleaved upon exposure to a pH of between about 11.3 and about 12.3, more particularly a pH of about 11.8.

Linkers can be cleaved or degraded under acidic, basic, oxidative, or reductive conditions. In a preferred embodiment, chemical cleavage is accomplished using a reducing agent, such as TCEP (tris(2-carboxyethyl) phosphine hydrochloride), β-mercaptoethanol, or DTT (dithiothreitol). In one embodiment, the linker is cleaved upon exposure to a solution having a pH ranging from about 11.3 to about 12.3. Optionally, the remaining portion of the linker is treated with an agent that renders it chemically unreactive.

Figure 2:
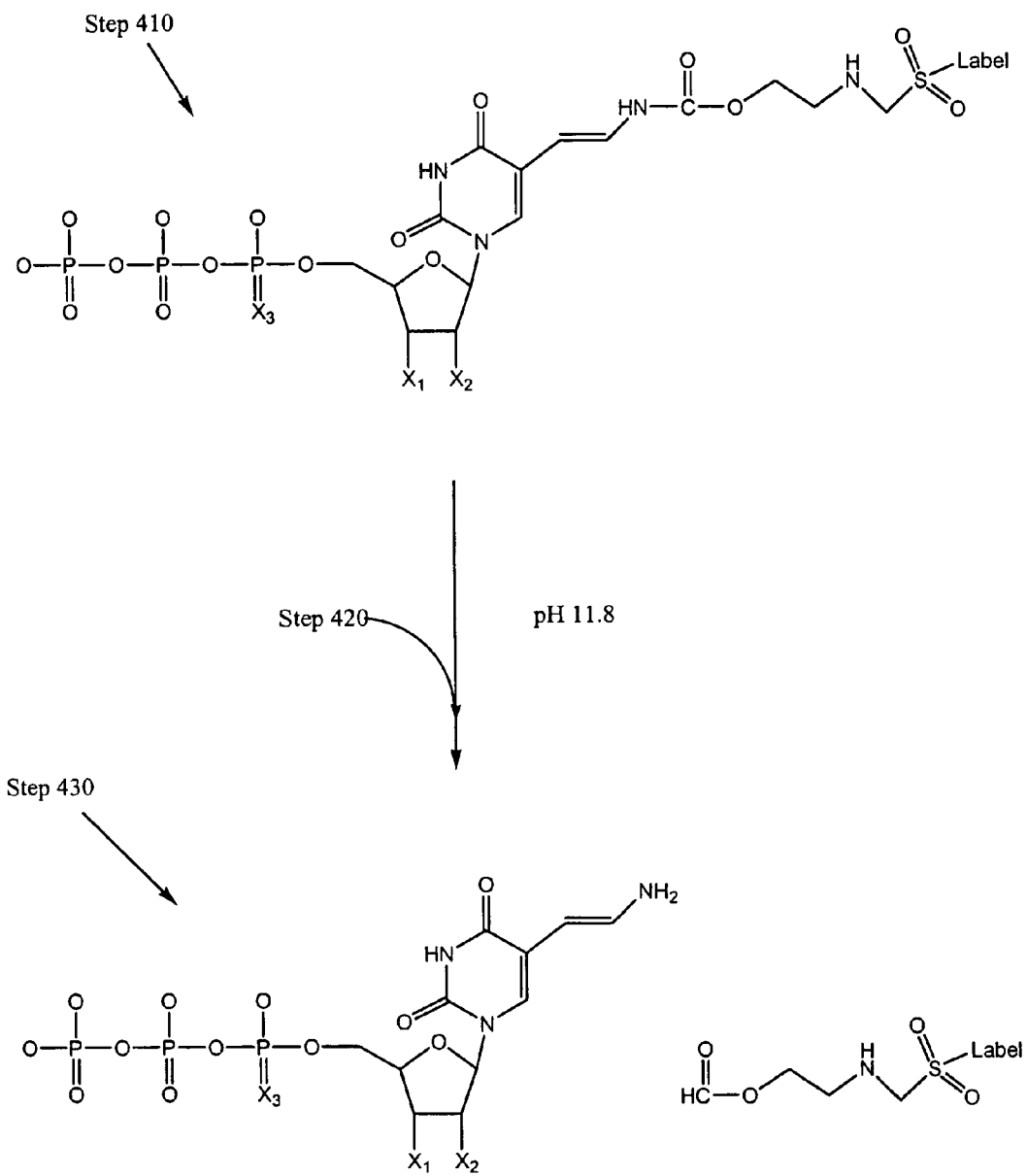
FIG. 2 shows exemplary chemical structures of nucleotide analogs of the present invention having a linker between the base and the label that undergo cleavage of the linker between the base and the label.

Referring now to FIG. 2. FIG. 2 shows a representation of a nucleotide analog of the invention having a linker featuring a carboxyl nitrogen bond between the base and the label, e.g., a dye. The carboxyl nitrogen bond is a cleavable site in the linker. In order to minimize structural perturbation of the base following cleavage, the cleavable site is located close to the base. Initiation and control of cleavage may be by, for example, chemical means (e.g., initiation by adding one or more chemical to alter the pH).

Specifically, referring still to FIG. 2, a nucleotide analog has a linker with a carboxyl nitrogen bond between the base and the label (Step 410). The linker features a cleavable site, a cleavable carboxyl nitrogen bond that when exposed to a pH of about 11.8 (Step 420) cleaves and removes the label and a portion of the linker. Specifically, upon exposure to a pH of about 11.8 the carboxyl, a portion of the linker, and the label are separated from a nitrogen that is attached to the base. The cleaved nitrogen bond bonds with a Hydrogen (e.g., a Hydrogen available in the solution having a pH of 11.8) and remains with the base (Step 430). Optionally, the linker remaining attached to the base may be reactive and can optionally be capped, rendering it unreactive.

Detection

Any detection method may be used to identify an incorporated nucleotide analog that is suitable for the type of label employed. Thus, exemplary detection methods include radioactive detection, optical absorbance detection, e.g., UV-visible absorbance detection, optical emission detection, e.g., fluorescence or chemiluminescence. Single-molecule fluorescence can be made using a conventional microscope equipped with total internal reflection (TIR) illumination. The detectable moiety associated with the extended primers can be detected on a substrate by scanning all or portions of each substrate simultaneously or serially, depending on the scanning method used. For fluorescence labeling, selected regions on a substrate may be serially scanned one-by-one or row-by-row using a fluorescence microscope apparatus, such as described in Fodor (U.S. Pat. No. 5,445,934) and Mathies et al. (U.S. Pat. No. 5,091,652). Devices capable of sensing fluorescence from a single molecule include scanning tunneling microscope (siM) and the atomic force microscope (AFM). Hybridization patterns may also be scanned using a CCD camera (e.g., Model TE/CCD512SF, Princeton Instruments, Trenton, N.J.) with suitable optics (Ploem, in Fluorescent and Luminescent Probes for Biological Activity Mason, T. G. Ed., Academic Press, Landon, pp. 1-11 (1993), such as described in Yershov et al., Proc. Natl. Aca. Sci. 93:4913 (1996), or may be imaged by TV monitoring. For radioactive signals, a phosphorimager device can be used (Johnston et al., Electrophoresis, 13:566, 1990; Drmanac et al., Electrophoresis, 13:566, 1992; 1993). Other commercial suppliers of imaging instruments include General Scanning Inc., (Watertown, Mass. on the World Wide Web at genscan.com), Genix Technologies (Waterloo, Ontario, Canada; on the World Wide Web at confocal.com), and Applied Precision Inc. Such detection methods are particularly useful to achieve simultaneous scanning of multiple attached target nucleic acids.

The present invention provides for detection of molecules from a single nucleotide to a single target nucleic acid molecule. A number of methods are available for this purpose. Methods for visualizing single molecules within nucleic acids labeled with an intercalating dye include, for example, fluorescence microscopy. For example, the fluorescent spectrum and lifetime of a single molecule excited-state can be measured. Standard detectors such as a photomultiplier tube or avalanche photodiode can be used. Full field imaging with a two-stage image intensified COD camera also can be used. Additionally, low noise cooled CCD can also be used to detect single fluorescent molecules.

The detection system for the signal may depend upon the labeling moiety used, which can be defined by the chemistry available. For optical signals, a combination of an optical fiber or charged couple device (CCD) can be used in the detection step. In those circumstances where the substrate is itself transparent to the radiation used, it is possible to have an incident light beam pass through the substrate with the detector located opposite the substrate from the target nucleic acid. For electromagnetic labeling moieties, various forms of spectroscopy systems can be used. Various physical orientations for the detection system are available and discussion of important design parameters is provided in the art.

A number of approaches can be used to detect incorporation of fluorescently-labeled nucleotides into a single nucleic acid molecule. Optical setups include near-field scanning microscopy, far-field confocal microscopy, wide-field epi-illumination, light scattering, dark field microscopy, photoconversion, single and/or multiphoton excitation, spectral wavelength discrimination, fluorophore identification, evanescent wave illumination, and total internal reflection fluorescence (TIRF) microscopy. In general, certain methods involve detection of laser-activated fluorescence using a microscope equipped with a camera. Suitable photon detection systems include, but are not limited to, photodiodes and intensified CCD cameras. For example, an intensified charge couple device (ICCD) camera can be used. The use of an ICCD camera to image individual fluorescent dye molecules in a fluid near a surface provides numerous advantages. For example, with an ICCD optical setup, it is possible to acquire a sequence of images (movies) of fluorophores.

Some embodiments of the present invention use TIRF microscopy for two-dimensional imaging. TIRF microscopy uses totally internally reflected excitation light and is well known in the art. See, e.g., the World Wide Web at nikon-instruments.jp/eng/page/products/tirf.aspx. In certain embodiments, detection is carried out using evanescent wave illumination and total internal reflection fluorescence microscopy. An evanescent light field can be set up at the surface, for example, to image fluorescently-labeled nucleic acid molecules. When a laser beam is totally reflected at the interface between a liquid and a solid substrate (e.g., a glass), the excitation light beam penetrates only a short distance into the liquid. The optical field does not end abruptly at the reflective interface, but its intensity falls off exponentially with distance. This surface electromagnetic field, called the "evanescent wave," can selectively excite fluorescent molecules in the liquid near the interface. The thin evanescent optical field at the interface provides low background and facilitates the detection of single molecules with high signal-to-noise ratio at visible wavelengths.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

I claim:

1. A nucleotide analog having the structure:

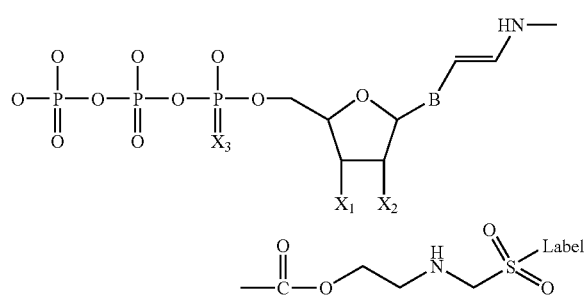

wherein $X_1$ is OH or $PO_4$; $X_2$ is H or OH; B is selected from the group consisting of a purine, a pyrimidine and derivatives thereof; $CH{=}CHNHC(O)OC_2H_4NHCH_2SO_2$ is a linker; and $X_3$ is O or S.

2. The nucleotide analog of claim 1, wherein said label is an optically-detectable label.

3. The nucleotide analog of claim 2, wherein said optically-detectable label is a fluorescent label.

4. The nucleotide analog of claim 1, wherein B is selected from the group consisting of cytosine, uracil, thymine, adenine, guanine, and analogs thereof.

5. The nucleotide analog of claim 1, wherein said linker comprises a cleavable bond.

6. The nucleotide analog of claim 5, wherein said cleavable bond is a chemically cleavable bond.

7. The nucleotide analog of claim 5, wherein said cleavable bond is a photochemically cleavable bond.

8. The nucleotide analog of claim 5, wherein said cleavable bond is cleaved upon exposure to a pH from about 11.3 to about 12.3.

9. The nucleotide analog of claim 5, wherein said cleavable bond is cleaved upon exposure to a pH of about 11.8.

10. A nucleotide analog having the structure:

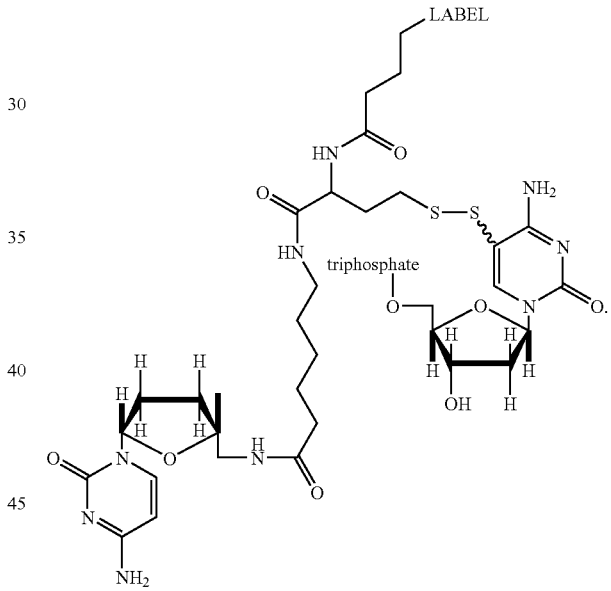

11. The nucleotide analog of claim 10, wherein said label is an optically-detectable label.

12. The nucleotide analog of claim 11, wherein said optically-detectable label is a fluorescent label.

* * * * *